United States Patent
Tsukamoto et al.

(10) Patent No.: US 8,187,838 B2
(45) Date of Patent: May 29, 2012

(54) β-GALACTOSIDE-α2, 6-SIALYLTRANSFERASE, A GENE ENCODING THEREOF, AND A METHOD FOR PRODUCING THEREOF

(75) Inventors: Hiroshi Tsukamoto, Iwata (JP); Toshiki Mine, Iwata (JP); Yoshimitsu Takakura, Iwata (JP); Takeshi Yamamoto, Iwata (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 12/789,167

(22) Filed: May 27, 2010

(65) Prior Publication Data

US 2010/0304460 A1 Dec. 2, 2010

Related U.S. Application Data

(62) Division of application No. 12/225,148, filed as application No. PCT/JP2006/315850 on Aug. 10, 2006.

(51) Int. Cl.
*C12P 21/02* (2006.01)

(52) U.S. Cl. ......... 435/69.1; 435/6; 435/7.1; 435/320.1; 435/252; 536/23.1; 530/350

(58) Field of Classification Search .................. None
See application file for complete search history.

(56) References Cited

U.S. PATENT DOCUMENTS

| | | | |
|---|---|---|---|
| 6,255,094 B1 | 7/2001 | Yamamoto et al. | |
| 7,884,066 B2 * | 2/2011 | Ting | 514/1.1 |
| 7,884,069 B2 * | 2/2011 | Schaebitz et al. | 530/399 |
| 7,884,263 B2 * | 2/2011 | Dewey et al. | 800/285 |

FOREIGN PATENT DOCUMENTS

| | | |
|---|---|---|
| EP | 0915163 A1 | 5/1999 |
| WO | WO-9838315 A1 | 9/1998 |

OTHER PUBLICATIONS

Seffernick et al. (J. Bacteriology, vol. 183, pp. 2405-2410, 2001).*
Wells (Biochemistry, vol. 29, pp. 8509-8517, 1990).*
Weinstein, J. et al., "Primary Structure of β-Galactoside α2,6-Sialyltransferase", The Journal of Biological Chemistry, vol. 262, No. 36, 1987, pp. 17735-17743.
Yamamoto, T. et al., "Cloning and Expression of a Marine Bacterial β-Galactoside α2,6-Sialyltransferase Gene from *Photobacterium damsela* JT0160", Journal of Biochemistry, vol. 123, No. 1, 1998, pp. 94-100.
Hamamoto, T. et al., "Two Step Single Primer Mediated Polymerase Chain Reaction.1 Application to Cloning of Putative Mouse, β-Galactoside α2,6-Sialyltransferase cDNA", Bioorganic & Medicinal Chemistry vol. 1, No. 2, pp. 141-145, 1993.
Yu, H. et al., "A Multifunctional Pasteurella multocida Sialytransferase: A Powerful Tool for the Synthesis of Sialoside Libraries", Journal of the American Chemical Society, vol. 127, No. 50, 2005, pp. 17618-17619.
Yamamoto, T. et al., "Mass Production of Bacterial α2,6-Sialytransferase and Enzymatic Syntheses of Sialyloligosaccharides", Biosci. Biotechnol. Biochem., vol. 62, No. 2, pp. 210-214, 1998, XP001069298.
Yamamoto, T. et al., "Purification and Characterization of a Marine Bacterial β-Galactoside α2,6-Sialyltransferase from *Photobacterium damsela* JT0160", Journal of Biochemistry, vol. 120, No. 1, 1996, pp. 104-110, XP001069919.

* cited by examiner

*Primary Examiner* — Hope Robinson
(74) *Attorney, Agent, or Firm* — Birch, Stewart, Kolasch & Birch, LLP

(57) ABSTRACT

The present invention provides a novel β-galactoside-α2,6-sialyltransferase having high productivity and/or high activity, and a nucleic acid encoding the sialyltransferase. The present invention also provides a microorganism producing the sialyltransferase. The present invention further provides a vector carrying a nucleic acid encoding the sialyltransferase, and a host cell transformed with the vector, as well as a method for producing a recombinant β-galactoside-α2,6-sialyltransferase.

10 Claims, 7 Drawing Sheets

β-GALACTOSIDE-α2, 6-SIALYLTRANSFERASE, A GENE ENCODING THEREOF, AND A METHOD FOR PRODUCING THEREOF

This application is a Divisional application of U.S. patent application Ser. No. 12/225,148, filed Jul. 20, 2009, which is a national stage application of International Application PCT/JP2006/315850 filed Aug. 10, 2006. U.S. patent application Ser. No. 12/225,148 also claims the benefit of foreign priority under 35 U.S.C. §119 of PCT/JP2006/304993, filed Mar. 14, 2006. The entire contents of the above-identified applications are hereby incorporated by reference.

TECHNICAL FIELD

The present invention relates to a novel β-galactoside-α2,6-sialyltransferase, a gene encoding the enzyme, a microorganism producing the enzyme and a method for producing the enzyme.

BACKGROUND ART

Glycosyltransferases are enzymes involved in in vivo biosynthesis of sugar chains on glycoproteins, glycolipids and the like (hereinafter referred to as "complex carbohydrates"). Their reaction products, i.e., sugar chains on complex carbohydrates have very important functions in the body. For example, sugar chains have been shown to be important molecules primarily in mammalian cells, which play a role in cell-cell and cell-extracellular matrix signaling and serve as tags for complex carbohydrates during differentiation and/or development.

Erythropoietin, a hormone for blood erythrocyte production, can be presented as an example where sugar chains are applied. Naturally-occurring erythropoietin is disadvantageous in that it has a short-lasting effect. Although erythropoietin is inherently a glycoprotein, further attempts have been made to add new sugar chains onto erythropoietin, as a result of which recombinant erythropoietin proteins with an extended in vivo life span have been developed and produced and are now commercially available. In the future, there will be increasing development of such products in which sugar chains are added or modified, including pharmaceuticals and functional foods. Thus, it is required to develop a means for freely synthesizing and producing sugar chains. In particular, the development of glycosyltransferases is increasing in importance as one of the most efficient means.

Until now, about 150 or more glycosyltransferase genes have been isolated from eukaryotic organisms including humans, mice, rats and yeast. Moreover, these genes have been expressed in host cells such as CHO cells or *E. coli* cells to produce proteins having glycosyltransferase activity. On the other hand, about 20 to 30 types of glycosyltransferase genes have also been isolated from bacteria which are prokaryotic organisms. Moreover, proteins having glycosyltransferase activity have been expressed in recombinant production systems using *E. coli* and identified for their substrate specificity and/or various enzymatic properties.

Sialic acid is often located at the nonreducing termini of sugar chains and is therefore regarded as a very important sugar in terms of allowing sugar chains to exert their functions. For this reason, sialyltransferase is one of the most in demand enzymes among glycosyltransferases. As to β-galactoside-α2,6-sialyltransferases and their genes, many reports have been issued for those derived from animals, particularly mammals (Hamamoto, T., et al., Bioorg. Med. Chem., 1, 141-145 (1993); Weinstein, J., et al., J. Biol. Chem., 262, 17735-17743 (1987)). However, such animal-derived enzymes are very expensive because they are difficult to purify and hence cannot be obtained in large amounts. Moreover, such enzymes have a problem in that they have poor stability as enzymes. In contrast, as to bacterial β-galactoside-α2,6-sialyltransferases and their genes, reports have been issued only for those isolated from microorganisms belonging to *Photobacterium damselae* (International Publication No. WO98/38315; U.S. Pat. No. 6,255,094).

However, *Photobacterium damselae*-derived β-galactoside-α2,6-sialyltransferase has a productivity of 550 U/L when produced from *Photobacterium damselae* (Yamamoto, T., et al., Biosci. Biotechnol. Biochem., 62(2), 210-214 (1998)), while the productivity is 224.5 U/L when this β-galactoside-α2,6-sialyltransferase is produced from *E. coli* cells transformed with plasmid pEBSTΔ178 carrying its gene (Yamamoto, T., et al., J. Biochem., 123, 94-100 (1998)). Thus, there is a demand for an enzyme having higher productivity. On the other hand, *Photobacterium damselae*-derived β-galactoside-α2,6-sialyltransferase has a specific activity of 5.5 U/mg (Yamamoto, T., et al., J. Biochem., 120, 104-110 (1996)). In this regard, there is also a demand for an enzyme having higher activity.

Among known bacterial sialyltransferases, *Pasteurella multocida*-derived α2,3-sialyltransferase can be listed as an enzyme whose productivity and activity are relatively high, although it is categorized as a different type of enzyme. This enzyme has a productivity of 6,000 U/L (Yu, H., et al., J. Am. Chem. Soc., 127, 17618-17619 (2005)) and a specific activity of 60 U/mg.

To meet the high demand of sialyltransferases, there is a need for β-galactoside-α2,6-sialyltransferases having higher productivity and/or activity.

Patent Document 1: International Publication No. WO98/38315
Patent Document 2: U.S. Pat. No. 6,255,094
Non-patent Document 1: Hamamoto, T., et al., Bioorg. Med. Chem., 1, 141-145 (1993)
Non-patent Document 2: Weinstein, J., et al., J. Biol. Chem., 262, 17735-17743 (1987)
Non-patent Document 3: Yamamoto, T., et al., Biosci. Biotechnol. Biochem., 62(2), 210-214 (1998)
Non-patent Document 4: Yamamoto, T., et al., J. Biochem., 123, 94-100 (1998)
Non-patent Document 5: Yamamoto, T., et al., J. Biochem., 120, 104-110 (1996)
Non-patent Document 6: Yu, H., et al., J. Am. Chem. Soc., 127, 17618-17619 (2005)

DISCLOSURE OF THE INVENTION

Problems to be Solved by the Invention

A problem to be solved by the present invention is to provide novel β-galactoside-α2,6-sialyltransferase derived from a microorganism belonging to the genus *Photobacterium* of the family Vibrionaceae, and a gene encoding the same. The present invention also aims to provide a novel β-galactoside-α2,6-sialyltransferase having higher productivity and/or higher activity than known bacterial sialyltransferases, and a gene encoding the same.

Another problem to be solved by the present invention is to provide a method for high production of the β-galactoside- α2,6-sialyltransferase of the present invention by gene recombination technology using a gene encoding this enzyme.

Means for Solving the Problems

As a result of extensive and intensive efforts made to separate and characterize 4,000 or more microbial strains from all areas of Japan, the inventors of the present invention have found a strain producing β-galactoside-α2,6-sialyltransferase activity from among strains of microorganisms belonging to the genus *Photobacterium*. The inventors have then cloned a novel α2,6-sialyltransferase gene from this strain by using as a probe the DNA of a known β-galactoside-α2,6-sialyltransferase gene from *Photobacterium damselae*. As a result of expressing this novel gene in *E. coli* cells, the inventors have found that this gene encodes a protein having β-galactoside-α2,6-sialyltransferase activity, and that the productivity of this enzyme is as high as about 10,700 U per liter of culture solution. As a result of further efforts to purify and analyze in detail this novel recombinant enzyme, the inventors have also found that this recombinant enzyme efficiently transfers sialic acid in α2,6 linkage to galactose, N-acetylgalactosamine or other residues in sugar chains, and that its specific activity is as high as about 110 U (unit)/mg to about 260 U/mg. In this way, the inventors have demonstrated many advantages over the known β-galactoside-α2,6-sialyltransferase derived from *Photobacterium damselae*, thereby completing the present invention. The present invention provides a novel β-galactoside-α2,6-sialyltransferase having high productivity and/or high activity, and a nucleic acid encoding the same, as well as a method for producing the sialyltransferase.

The present invention will now be illustrated in detail below.

β-Galactoside-α2,6-sialyltransferase

The present invention provides a novel β-galactoside-α2,6-sialyltransferase. As used herein, the term "β-galactoside-α2,6-sialyltransferase" is intended to mean a protein having the ability to transfer sialic acid from cytidine monophosphate (CMP)-sialic acid to the 6-position of a galactose residue in complex carbohydrate sugar chains or free sugar chains, to the 6-position of galactose present in oligosaccharides such as lactose or N-acetyllactosamine, or to the 6-position of a monosaccharide (e.g., galactose, N-acetylgalactosamine, glucose, N-acetylglucosamine or mannose) which may be used as a constituting member of complex carbohydrates and has a hydroxyl group on the carbon at the 6-position. As used herein, the term "β-galactoside-α2,6-sialyltransferase activity" is intended to mean the ability described above for β-galactoside-α2,6-sialyltransferase. The term "sialic acid" as used herein refers to a neuraminic acid derivative belonging to the sialic acid family. More specifically, it refers to N-acetylneuraminic acid (Neu5Ac), N-glycolylneuraminic acid (Neu5Gc), 5-deamino-5-hydroxyneuraminic acid (KDN), disialic acid (i.e., di-N-acetylneuraminic acid; Neu5Acα2,8(9)Neu5Ac) or the like.

The β-galactoside-α2,6-sialyltransferase of the present invention is a protein comprising the amino acid sequence shown in SEQ ID NO: 2, SEQ ID NO: 4 or SEQ ID NO: 12. The amino acid sequence shown in SEQ ID NO: 4 corresponds to a sequence having methionine at the N-terminus of an amino acid sequence covering amino acids 18-514 of SEQ ID NO: 2. The amino acid sequence shown in SEQ ID NO: 12 corresponds to a sequence having methionine at the N-terminus of an amino acid sequence covering amino acids 111-514 of SEQ ID NO: 2. This N-terminal methionine is derived from the initiation codon for protein expression and does not affect the activity of β-galactoside-α2,6-sialyltransferase. Moreover, the N-terminal methionine in a protein may often be cleaved off by intracellular processing. Thus, a protein comprising the amino acid sequence shown in SEQ ID NO: 4 includes not only a protein comprising an amino acid sequence completely identical with SEQ ID NO: 4, but also a protein comprising an amino acid sequence lacking the N-terminal methionine.

As described later in Example 2, ISH224-N1C0/pTrc (SEQ ID NO: 4; a sequence having methionine at the N-terminus of an amino acid sequence covering amino acids 18-514 of SEQ ID NO: 2) and ISH224-N3C0/pTrc (SEQ ID NO: 12; a sequence having methionine at the N-terminus of an amino acid sequence covering amino acids 111-514 of SEQ ID NO: 2) both retained the activity of β-galactoside-α2,6-sialyltransferase derived from the strain JT-ISH-224. Thus, the presence of at least amino acids 111-514 of SEQ ID NO: 2 allows retention of β-galactoside-α2,6-sialyltransferase activity. For this reason, the "protein comprising the amino acid sequence shown in SEQ ID NO: 12" according to the present invention includes a protein comprising an amino acid sequence lacking all or part of amino acids 1-110 from amino acids 1-514 of SEQ ID NO: 2.

Alternatively, the β-galactoside-α2,6-sialyltransferase of the present invention is a protein encoded by a nucleic acid comprising the nucleotide sequence shown in SEQ ID NO: 1, SEQ ID NO: 3 or SEQ ID NO: 11. The nucleotide sequence shown in SEQ ID NO: 3 corresponds to a sequence having an initiation codon (ATG) at the 5'-terminus of a nucleotide sequence covering nucleotides 52-1545 of SEQ ID NO: 1. The nucleotide sequence shown in SEQ ID NO: 11 corresponds to a sequence having an initiation codon (ATG) at the 5'-terminus of a nucleotide sequence covering nucleotides 331-1545 of SEQ ID NO: 1. The nucleotide sequences shown in SEQ ID NO: 1, SEQ ID NO: 3 and SEQ ID NO: 11 encode the amino acid sequences of SEQ ID NO: 2, SEQ ID NO: 4 and SEQ ID NO: 12, respectively.

In the β-galactoside-α2,6-sialyltransferase of the present invention comprising the amino acid sequence shown in SEQ ID NO: 2, a sequence covering amino acids 12-15 of SEQ ID NO: 2 is Leu-Thr-Ala-Cys, which is a consensus sequence called lipobox, so that cleavage will occur within bacterial cells at the amino terminus of Cys in this consensus sequence (Madan Babu, M. and Sankaran, K. Bioinformatics. 18, 641-643 (2002)). Thus, the β-galactoside-α2,6-sialyltransferase of the present invention may be a protein comprising an amino acid sequence covering amino acids 15-514 of SEQ ID NO: 2. Alternatively, the β-galactoside-α2,6-sialyltransferase of the present invention may be a protein encoded by a nucleic acid comprising a nucleotide sequence covering nucleotides 43-1545 of SEQ ID NO: 1.

The present invention also encompasses mutants of the above β-galactoside-α2,6-sialyltransferases of the present invention, i.e., mutated proteins having β-galactoside-α2,6-sialyltransferase activity. Such mutated proteins also fall within the scope of the β-galactoside-α2,6-sialyltransferase of the present invention.

The mutant protein of the present invention may be a protein having β-galactoside-α2,6-sialyltransferase activity, which comprises an amino acid sequence comprising deletion, substitution, insertion and/or addition of one or more amino acids in an amino acid sequence selected from the group consisting of SEQ ID NO: 2, amino acids 15-514 of SEQ ID NO: 2, SEQ ID NO: 4 and SEQ ID NO: 12. The substitution may be conservative, which means the replacement of a certain amino acid residue by another residue having similar physical and chemical characteristics. Non-limiting examples of conservative substitution include replacement between aliphatic group-containing amino acid residues such as Ile, Val, Leu or Ala, and replacement between polar residues such as Lys-Arg, Glu-Asp or Gln-Asn replacement.

Mutants derived by amino acid deletion, substitution, insertion and/or addition can be prepared when DNAs encoding their wild-type proteins are subjected to, for example, well-known site-directed mutagenesis (see, e.g., Nucleic Acid Research, Vol. 10, No. 20, p. 6487-6500, 1982, which is hereby incorporated by reference in its entirety). As used herein, the term "one or more amino acids" is intended to mean a possible number of amino acids which may be deleted, substituted, inserted and/or added by site-directed mutagenesis.

Site-directed mutagenesis may be accomplished, for example, as follows using a synthetic oligonucleotide primer that is complementary to single-stranded phage DNA to be mutated, except for having a specific mismatch (i.e., a desired mutation). Namely, the above synthetic oligonucleotide is used as a primer to cause synthesis of a complementary strand by phages, and the resulting duplex DNA is then used to transform host cells. The transformed bacterial culture is plated on agar, whereby plaques are allowed to form from phage-containing single cells. As a result, in theory, 50% of new colonies contain phages with the mutation as a single strand, while the remaining 50% have the original sequence. At a temperature which allows hybridization with DNA completely identical to one having the above desired mutation, but not with DNA having the original strand, the resulting plaques are allowed to hybridize with a synthetic probe labeled by kinase treatment. Subsequently, plaques hybridized with the probe are picked up and cultured for collection of their DNA.

Techniques for allowing deletion, substitution, insertion and/or addition of one or more amino acids in the amino acid sequences of biologically active peptides such as enzymes while retaining their activity include site-directed mutagenesis mentioned above, as well as other techniques such as those for treating a gene with a mutagen, and those in which a gene is selectively cleaved to remove, substitute, insert or add a selected nucleotide or nucleotides, and then ligated.

The mutant protein of the present invention may also be a protein having β-galactoside-α2,6-sialyltransferase activity, which is encoded by a nucleic acid comprising a nucleotide sequence comprising deletion, substitution, insertion and/or addition of one or more nucleotides in a nucleotide sequence selected from the group consisting of SEQ ID NO: 1, nucleotides 43-1545 of SEQ ID NO: 1, SEQ ID NO: 3 and SEQ ID NO: 11. Nucleotide deletion, substitution, insertion and/or addition may be accomplished by site-directed mutagenesis or other techniques as mentioned above.

The mutant protein of the present invention may further be a protein having β-galactoside-α2,6-sialyltransferase activity, which comprises an amino acid sequence sharing an amino acid identity of at least 60% or more, preferably 65% or more, 70% or more, 75% or more, 80% or more, 85% or more, 90% or more, 95% or more, 98% or more, or 99% or more, and more preferably 99.5% or more with an amino acid sequence selected from the group consisting of SEQ ID NO: 2, amino acids 15-514 of SEQ ID NO: 2, SEQ ID NO: 4 and SEQ ID NO: 12.

Alternatively, the mutant protein of the present invention may be a protein having β-galactoside-α2,6-sialyltransferase activity, which is encoded by a nucleic acid sharing an identity of at least 70% or more, preferably 75% or more, 80% or more, 85% or more, 90% or more, 95% or more, 98% or more, or 99% or more, and more preferably 99.5% or more with a nucleotide sequence selected from the group consisting of SEQ ID NO: 1, nucleotides 43-1545 of SEQ ID NO: 1, SEQ ID NO: 3 and SEQ ID NO: 11.

The percent identity between two amino acids may be determined by visual inspection and mathematical calculation. Alternatively, the percent identity of two protein sequences may be determined by comparing sequence information based on the algorithm of Needleman, S. B. and Wunsch, C. D. (J. Mol. Biol., 48:443-453, 1970) and using the GAP computer program available from the University of Wisconsin Genetics Computer Group (UWGCG). The preferred default parameters for the GAP program include: (1) a scoring matrix, blosum62, as described by Henikoff, S. and Henikoff, J. G. (Proc. Natl. Acad. Sci. USA, 89:10915-10919, 1992); (2) a gap weight of 12; (3) a gap length weight of 4; and (4) no penalty for end gaps.

Other programs used by those skilled in the art of sequence comparison may also be used. The percent identity can be determined by comparing sequence information using, e.g., the BLAST program described by Altschul et al. (Nucl. Acids. Res., 25, p. 3389-3402, 1997). This program is available on the Internet at the web site of the National Center for Biotechnology Information (NCBI) or the DNA Data Bank of Japan (DDBJ). The details of various conditions (parameters) for identity search using the BLAST program are shown on these web sites, and default values are commonly used for search although part of the settings may be changed as appropriate. Alternatively, the percent identity of two amino acid sequences may be determined by using a program such as genetic information processing software GENETYX Ver.7 (Genetyx Corporation, Japan) or using an algorithm such as FASTA. In this case, default values may be used for search.

The percent identity between two nucleic acid sequences can be determined by visual inspection and mathematical calculation, or more preferably, the comparison is done by comparing sequence information using a computer program. An exemplary, preferred computer program is the Genetic Computer Group (GCG; Madison, Wis.) Wisconsin package version 10.0 program, "GAP" (Devereux et al., 1984, Nucl. Acids Res., 12:387). In addition to making a comparison between two nucleic acid sequences, this "GAP" program can be used for comparison between two amino acid sequences and between a nucleic acid sequence and an amino acid sequence. The preferred default parameters for the "GAP" program include: (1) the GCG implementation of a unary comparison matrix (containing a value of 1 for identities and 0 for non-identities) for nucleotides, and the weighted amino acid comparison matrix of Gribskov and Burgess, Nucl. Acids Res., 14:6745, 1986, as described by Schwartz and Dayhoff, eds., "Atlas of Polypeptide Sequence and Structure," National Biomedical Research Foundation, pp. 353-358, 1979, or other comparable comparison matrices; (2) a penalty of 30 for each gap and an additional penalty of 1 for each symbol in each gap for amino acid sequences, or penalty of 50 for each gap and an additional penalty of 3 for each symbol in each gap for nucleotide sequences; (3) no penalty for end gaps; and (4) no maximum penalty for long gaps. Other programs used by those skilled in the art of sequence comparison can also be used, such as, for example, the BLASTN program version 2.2.7, available for use via the National Library of Medicine website: www.ncbi.nlm.nih.gov/blast/b12seq/bls.html, or the UW-BLAST 2.0 algorithm. Standard default parameter settings for UW-BLAST 2.0 are described at the following Internet site: http://blast.wustl.edu blast.wustl.edu. In addition, the BLAST algorithm uses the BLOSUM62 amino acid scoring matrix, and optional parameters that can be used are as follows: (A) inclusion of a filter to mask segments of the query sequence that have low compositional complexity (as determined by the SEG program of Wootton and Federhen (Computers and Chemistry, 1993); also see Wootton and Federhen, 1996, "Analysis of compositionally biased regions in sequence databases," Methods Enzymol., 266: 554-71) or segments consisting of short-periodicity internal repeats (as determined by the XNU program of Clayerie and States (Computers and Chemistry, 1993)), and (B) a statistical significance threshold for reporting matches against database sequences, or E-score (the expected probability of matches being found merely by chance, according to the stochastic model of Karlin and Altschul, 1990; if the statistical significance ascribed to a match is greater than this E-score threshold, the match will not be reported.); preferred E-score threshold values are 0.5, or in order of increasing preference, 0.25, 0.1, 0.05, 0.01, 0.001, 0.0001, 1e-5, 1e-10, 1e-15, 1e-20, 1e-25, 1e-30, 1e-40, 1e-50, 1e-75, or 1e-100.

The mutant protein of the present invention may also be a protein having β-galactoside-α2,6-sialyltransferase activity, which is encoded by a nucleic acid comprising a nucleotide sequence hybridizable under stringent conditions with the complementary strand of a nucleotide sequence selected from the group consisting of SEQ ID NO: 1, nucleotides 43-1545 of SEQ ID NO: 1, SEQ ID NO: 3 and SEQ ID NO: 11.

The term "under stringent condition" means that two sequences hybridize under moderately or highly stringent conditions. More specifically, moderately stringent conditions can be readily determined by those having ordinary skill in the art, e.g., depending on the length of DNA. The basic conditions are set forth by Sambrook et al., Molecular Cloning: A Laboratory Manual, third edition, chapters 6 and 7, Cold Spring Harbor Laboratory Press, 2001 and include the use of a prewashing solution for nitrocellulose filters 5×SSC, 0.5% SDS, 1.0 mM EDTA (pH 8.0), hybridization conditions of about 50% formamide, 2×SSC to 6×SSC at about 40-50° C. (or other similar hybridization solutions, such as Stark's solution, in about 50% formamide at about 42° C.) and washing conditions of, for example, about 40-60° C., 0.5-6×SSC, 0.1% SDS. Preferably, moderately stringent conditions include hybridization (and washing) at about 50° C. and 6×SSC. Highly stringent conditions can also be readily determined by those skilled in the art, e.g., depending on the length of DNA.

Generally, such conditions include hybridization and/or washing at higher temperature and/or lower salt concentration (such as hybridization at about 65° C., 6×SCC to 0.2× SSC, preferably 6×SCC, more preferably 2×SSC, most preferably 0.2×SSC), compared to the moderately stringent conditions. For example, highly stringent conditions may include hybridization as defined above, and washing at approximately 65-68° C., 0.2×SSC, 0.1% SDS. SSPE (1×SSPE is 0.15 M NaCl, 10 mM NaH$_2$PO$_4$, and 1.25 mM EDTA, pH 7.4) can be substituted for SSC (1×SSC is 0.15 M NaCl and 15 mM sodium citrate) in the hybridization and washing buffers; washing is performed for 15 minutes after hybridization is completed.

It is also possible to use a commercially available hybridization kit which uses no radioactive substance as a probe. Specific examples include hybridization with an ECL direct labeling & detection system (Amersham). Stringent conditions include, for example, hybridization at 42° C. for 4 hours using the hybridization buffer included in the kit, which is supplemented with 5% (w/v) Blocking reagent and 0.5 M NaCl, and washing twice in 0.4% SDS, 0.5×SSC at 55° C. for 20 minutes and once in 2×SSC at room temperature for 5 minutes.

Sialyltransferase activity may be measured by known procedures, e.g., those described in J. Biochem., 120, 104-110 (1996) (which is hereby incorporated by reference in its entirety). For example, the enzyme activity can be evaluated by effecting an enzymatic reaction using CMP-NeuAc (N-acetylneuraminic acid) as a glycosyl donor substrate and lactose as a glycosyl acceptor substrate, followed by evaluating the amount of the reaction product sialyllactose. It should be noted that one enzyme unit (1U) is defined as the amount of enzyme required to transfer 1 micromole of sialic acid per minute.

Determination of the binding mode of sialic acid transferred to a glycosyl acceptor substrate may be accomplished by using, but not limited to, any procedure known to those skilled in the art, such as those using a pyridylaminated sugar chain or reaction product analysis by nuclear magnetic resonance spectroscopy (NMR). Procedures using a pyridylaminated sugar chain comprise effecting an enzymatic reaction using a pyridylaminated sugar chain as a glycosyl acceptor substrate. More specifically, an enzymatic reaction is effected using pyridylaminated lactose (Galβ1-4Glc-PA, Takara Bio Inc., Japan) as a glycosyl acceptor substrate and CMP-NeuAc as a glycosyl donor substrate, and the reaction product is subjected to high performance liquid chromatography (HPLC) analysis. From the retention time of the reaction product, the position at which sialic acid was transferred is identified.

In an embodiment of the present invention, the enzyme of the present invention is derived from microorganisms belonging to the genus *Photobacterium*. The enzyme of the present invention is not limited in any way as long as it is derived from microorganisms belonging to the genus *Photobacterium*. It may be an enzyme derived from a new species of microorganism belonging to the genus *Photobacterium*.

As to enzymological properties as well as physical and chemical properties, the β-galactoside-α2,6-sialyltransferase of the present invention is not only characterized by having β-galactoside-α2,6-sialyltransferase activity as defined above, but also has additional properties including, but not limited to: an optimum pH ranging from 5 to 6; an optimum temperature of 25° C. to 35° C.; and a molecular weight of about 56,000±3,000 Da, as measured by SDS-PAGE analysis.

Moreover, in an embodiment, the β-galactoside-α2,6-sialyltransferase of the present invention is characterized by having high β-galactoside-α2,6-sialyltransferase activity. As used herein, the term "high β-galactoside-α2,6-sialyltransferase activity" is intended to mean having activity of 6 U or more, 10 U or more, 20 U or more, 40 U or more, 60 U or more, or 100 U or more per mg of enzyme.

Nucleic Acid Encoding
β-galactoside-α2,6-sialyltransferase

The present invention provides a nucleic acid encoding β-galactoside-α2,6-sialyltransferase.

The nucleic acid of the present invention is a nucleic acid encoding a protein comprising an amino acid sequence selected from the group consisting of SEQ ID NO: 2, amino acids 15-514 of SEQ ID NO: 2, SEQ ID NO: 4 and SEQ ID NO: 12. Alternatively, the nucleic acid of the present invention is a nucleic acid comprising a nucleotide sequence selected from the group consisting of SEQ ID NO: 1, nucleotides 43-1545 of SEQ ID NO: 1, SEQ ID NO: 3 and SEQ ID NO: 11.

The nucleic acid of the present invention may be a mutant of the above nucleic acid as long as it is a nucleic acid encoding a protein having β-galactoside-α2,6-sialyltransferase activity. Such a nucleic acid also falls within the scope of the nucleic acid of the present invention encoding β-galactoside-α2,6-sialyltransferase.

Such a nucleic acid mutant is a nucleic acid encoding a protein having β-galactoside-α2,6-sialyltransferase activity, wherein the protein comprises an amino acid sequence comprising deletion, substitution, insertion and/or addition of one or more amino acids in an amino acid sequence selected from the group consisting of SEQ ID NO: 2, amino acids 15-514 of SEQ ID NO: 2, SEQ ID NO: 4 and SEQ ID NO: 12. The nucleic acid mutant of the present invention is also a nucleic acid comprising a nucleotide sequence comprising deletion, substitution, insertion and/or addition of one or more nucleotides in a nucleotide sequence selected from the group consisting of SEQ ID NO: 1, nucleotides 43-1545 of SEQ ID NO: 1, SEQ ID NO: 3 and SEQ ID NO: 11. Amino acid or nucleotide deletion, substitution, insertion and/or addition can be introduced as described above.

Alternatively, such a nucleic acid mutant is a nucleic acid encoding a protein having β-galactoside-α2,6-sialyltransferase activity, wherein the protein comprises an amino acid sequence sharing an identity of at least 60% or more, preferably 65% or more, 70% or more, 75% or more, 80% or more, 85% or more, 90% or more, 95% or more, 98% or more, or 99% or more, and more preferably 99.5% or more with an amino acid sequence selected from the group consisting of SEQ ID NO: 2, amino acids 15-514 of SEQ ID NO: 2, SEQ ID NO: 4 and SEQ ID NO: 12. The nucleic acid mutant of the present invention is also a nucleic acid encoding a protein having β-galactoside-α2,6-sialyltransferase activity, wherein the nucleic acid shares an identity of preferably 70% or more, 75% or more, 80% or more, 85% or more, 90% or more, 95% or more, 98% or more, or 99% or more, and more preferably 99.5% or more with a nucleotide sequence selected from the group consisting of SEQ ID NO: 1, nucleotides 43-1545 of SEQ ID NO: 1, SEQ ID NO: 3 and SEQ ID NO: 11. In this case, the identity between amino acid sequences or nucleotide sequences can be determined as described above.

Such a nucleic acid mutant is further a nucleic acid encoding a protein having β-galactoside-α2,6-sialyltransferase activity, wherein the nucleic acid comprises a nucleotide sequence hybridizable under stringent conditions or highly stringent conditions with the complementary strand of a nucleotide sequence selected from the group consisting of SEQ ID NO: 1, nucleotides 43-1545 of SEQ ID NO: 1, SEQ ID NO: 3 and SEQ ID NO: 11. In this case, stringent conditions or highly stringent conditions are as defined above.

Microorganisms Expressing
β-galactoside-α2,6-sialyltransferase

The inventors of the present invention have found that microorganisms belonging to the genus *Photobacterium* of the family Vibrionaceae express a novel β-galactoside-α2,6-sialyltransferase. Thus, the present invention provides microorganisms expressing β-galactoside-α2,6-sialyltransferase. The microorganisms of the present invention are those belonging to the genus *Photobacterium* and having the ability to produce β-galactoside-α2,6-sialyltransferase. Examples of microorganisms belonging to the genus *Photobacterium* and having the ability to produce β-galactoside-α2,6-sialyltransferase include *Photobacterium* sp. strain JT-ISH-224 (Accession No. NITE BP-87). It should be noted that the above microorganisms of the genus *Photobacterium* are generally marine bacteria, which are separated from sea water or marine products such as fish and shellfish. For example, *Photobacterium* sp. strain JT-ISH-224 of the present invention was separated from barracuda in Ishikawa prefecture.

The microorganisms of the present invention can be separated using screening procedures as shown below, by way of example. Sea water, sea sand, sea mud or a marine product is used as a microorganism source. Sea water, sea sand and sea mud may be used directly or further diluted with sterilized sea water for use as an inoculum. In the case of small marine animals, their surface slime or the like is collected by scrubbing with a loop and is then used as an inoculum; or alternatively, their internal organs are homogenized in sterilized sea water and the resulting fluid is used as an inoculum. These inocula are applied onto agar plates such as marine broth agar 2216 medium (Becton Dickinson) or sodium chloride-supplemented nutrient agar medium (Becton Dickinson) to obtain marine microorganisms growing under various temperature conditions. After the resulting microorganisms have been pure-cultured in a routine manner, each microorganism is cultured using a liquid medium such as marine broth 2216 medium (Becton Dickinson) or sodium chloride-supplemented nutrient broth medium (Becton Dickinson). After the microorganisms are fully grown, the cells are collected by centrifugation from each culture solution. To the collected cells, 20 mM cacodylate buffer (pH 6.0) containing 0.2% Triton® X-100 (Kanto Kagaku, Japan) is added, and the cells are suspended therein. This cell suspension is ultrasonicated under ice cooling to homogenize the cells. This cell homogenate is used as an enzyme solution and measured for its sialyltransferase activity in a routine manner, to thereby obtain a strain having sialyltransferase activity.

The above screening procedures were also used for obtaining *Photobacterium* sp. strain JT-ISH-224 of the present invention. Its microbiological properties as well as physiological and biochemical properties will be detailed in Example 1, along with species identification based on nucleotide sequence analysis of the 16S-rRNA gene.

*Photobacterium* sp. strain JT-ISH-224 was deposited under the Budapest Treaty on Mar. 11, 2005 under NITE BP-87 with the National Institute of Technology and Evaluation, Patent Microorganisms Depositary (NPMD; 2-5-8 Kazusakamatari, Kisarazu, Chiba, Japan).

Method for Producing
β-galactoside-α2,6-sialyltransferase

The present invention also relates to a method for producing the β-galactoside-α2,6-sialyltransferase of the present invention. In a preferred embodiment, the method of the present invention allows high production of the enzyme of the present invention. More specifically, the productivity of the enzyme of the present invention in the method of the present invention is 50 U/L or more, 1,000 U/L or more, or 10,000 U/L or more per liter of culture solution.

(1) Method for Producing β-galactoside-α2,6-sialyltransferase by Culturing Microorganisms Expressing the Enzyme In an embodiment of the present invention, the β-galactoside-α2,6-sialyltransferase of the present invention is derived from microorganisms belonging to the genus *Photobacterium*, and is obtained as follows: a microorganism having the ability to produce β-galactoside-α2,6-sialyltransferase is cultured in a medium and allowed to produce β-galactoside-α2, 6-sialyltransferase, which is then collected.

Microorganisms used for this purpose are not limited in any way as long as they belong to the genus *Photobacterium* and have the ability to produce β-galactoside-α2,6-sialyltransferase. Preferred are those belonging to *Photobacterium* spp. Examples of microorganisms for use in the method of the present invention include *Photobacterium* sp. strain JT-ISH-224 (Accession No. NITE BP-87).

For use in culturing the above microorganisms, the culture medium contains ingredients available to these microorganisms, including a carbon source, a nitrogen source and minerals. Such a carbon source includes peptone, tryptone, casein lysate, meat extract and glucose, with peptone being preferred for use. As a nitrogen source, yeast extract is preferred for use. Salts include sodium chloride, iron citrate, magnesium chloride, sodium sulfate, calcium chloride, potassium chloride, sodium carbonate, sodium bicarbonate, potassium bromide, strontium chloride, sodium borate, sodium silicate, sodium fluoride, ammonium nitrate and disodium hydrogen phosphate, which are preferably used in combination as appropriate.

Alternatively, marine broth 2216 medium (Becton Dickinson) containing the above ingredients may be used. Further, artificial sea water containing the above salts in appropriate amounts may also be used, supplemented with peptone, yeast extract or the like. Culture conditions will somewhat vary depending on the medium composition and/or the type of strain. For example, in the case of culturing *Photobacterium* sp. strain JT-ISH-224, the culture temperature is about 20° C. to 30° C., preferably about 25° C. to 30° C., and the culture period is about 6 to 48 hours, preferably about 15 to 24 hours.

Since a target enzyme exists within cells, any of known cell homogenization techniques such as ultrasonic disruption, French press homogenization, glass bead homogenization or Dynomil homogenization can be performed to separate and purify the target enzyme from the resulting cell homogenate. In the method of the present invention, a preferred cell homogenization technique is ultrasonic disruption. For example, after centrifugation to remove solid matter from the cell homogenate, the resulting cell homogenate supernatant can be purified, e.g., by column chromatography on a commercially available column such as an anion exchange column, a cation exchange column, a gel filtration column, a hydroxyapatite column, a CDP-hexanolamine agarose column, a CMP-hexanolamine agarose column and/or a hydrophobic column, as well as Native-PAGE, which are used in combination as appropriate.

It should be noted that although β-galactoside-α2,6-sialyltransferase may be completely purified, the β-galactoside-α2,6-sialyltransferase of the present invention may be in either purified or partially purified form because it has sufficient activity even in partially purified form.

(2) Method for Producing Recombinant β-galactoside-α2,6-sialyltransferase

The present invention provides an expression vector carrying a nucleic acid encoding β-galactoside-α2,6-sialyltransferase, and a host cell containing the expression vector. Moreover, the present invention also provides a method for producing a recombinant β-galactoside-α2,6-sialyltransferase protein, which comprises culturing a host cell containing the expression vector under conditions suitable for recombinant protein expression, and collecting the expressed recombinant protein.

To produce the recombinant β-galactoside-α2,6-sialyltransferase protein of the present invention, an expression vector chosen depending on the host to be used is inserted with a nucleic acid sequence encoding β-galactoside-α2,6-sialyltransferase that is operably linked to a suitable transcription or translation regulatory nucleotide sequence derived from a gene of mammalian, microorganism, viral, insect or other origin. Examples of such a regulatory sequence include a transcription promoter, an operator or an enhancer, a mRNA ribosome binding site, as well as suitable sequences regulating the initiation and termination of transcription and translation.

Such a nucleic acid sequence encoding β-galactoside-α2,6-sialyltransferase to be inserted into the vector of the present invention is a nucleotide sequence of the above nucleic acid of the present invention encoding β-galactoside-α2,6-sialyltransferase, which may or may not comprise a leader sequence. When the nucleotide sequence comprises a leader sequence, it may be a leader sequence corresponding to nucleotides 1-42 of SEQ ID NO: 1, or may be replaced by a leader sequence derived from other organisms. Leader sequence replacement enables the design of an expression system which allows secretion of the expressed protein into the extracellular environment of host cells.

Moreover, the recombinant β-galactoside-α2,6-sialyltransferase protein of the present invention may also be expressed as a fusion protein by inserting a vector with a nucleic acid designed such that a nucleic acid encoding a His tag, a FLAG™ tag, glutathione-S-transferase or the like is linked downstream of a nucleic acid encoding the enzyme. When the enzyme of the present invention is expressed as a fusion protein in this way, such a fusion protein can facilitate purification and detection of the enzyme.

Host cells suitable for protein expression of β-galactoside-α2,6-sialyltransferase include prokaryotic cells, yeast or higher eukaryotic cells. Suitable cloning and expression vectors for use in bacterial, fungal, yeast and mammalian host cells are described, for example, in Pouwels et al., Cloning Vectors: A Laboratory Manual, Elsevier, New York, (1985) (which is hereby incorporated by reference in its entirety).

Prokaryotic organisms include Gram-negative or Gram-positive bacteria such as *E. coli* or *Bacillus subtilis*. When a prokaryotic cell such as *E. coli* is used as a host, a β-galactoside-α2,6-sialyltransferase protein may be designed to have an N-terminal methionine residue for the purpose of facilitating recombinant polypeptide expression within prokaryotic cells. This N-terminal methionine may be cleaved from the expressed recombinant α2,6-sialyltransferase protein.

Expression vectors for use in prokaryotic host cells generally contain one or more phenotype selectable marker genes. Such a phenotype selectable marker gene is, for example, a gene imparting antibiotic resistance or auxotrophy. Examples of expression vectors suitable for prokaryotic host cells include commercially available plasmids such as pBR322 (ATCC37017) or derivatives thereof. pBR322 contains genes for ampicillin and tetracycline resistance, and thereby facilitates identification of transformed cells. DNA sequences of a suitable promoter and a nucleic acid encoding β-galactoside-α2,6-sialyltransferase are inserted into this pBR322 vector. Other commercially available vectors include, for example, pKK223-3 (Pharmacia Fine Chemicals, Uppsala, Sweden) and pGEM1 (Promega Biotech., Madison, Wis., United States).

Promoter sequences generally used in expression vectors for prokaryotic host cells include tac promoter, β-lactamase (penicillinase) promoter, and lactose promoter (Chang et al., Nature 275:615, 1978; and Goeddel et al., Nature 281:544, 1979, which are hereby incorporated by reference in their entirety).

Alternatively, a recombinant β-galactoside-α2,6-sialyltransferase protein may be expressed in yeast host cells, preferably using *Saccharomyces* (e.g., *S. cerevisiae*). Other genera of yeast, such as *Pichia* or *Kluyveromyces*, may also be used. Yeast vectors often contain an origin of replication sequence from 2µ yeast plasmid, an autonomously replicating sequence (ARS), a promoter region, sequences for polyadenylation, sequences for transcription termination, and a selectable marker gene. A yeast α-factor leader sequence can also be used to induce secretion of a recombinant β-galactoside-α2,6-sialyltransferase protein. There are also known other leader sequences that are suitable for facilitating recombinant polypeptide secretion from yeast hosts. Procedures for yeast transformation are described, for example, in Hinnen et al., Proc. Natl. Acad. Sci. USA, 75: 1929-1933, 1978 (which is hereby incorporated by reference in its entirety).

Mammalian or insect host cell culture systems can also be used to express a recombinant β-galactoside-α2,6-sialyltransferase protein. Established cell lines of mammalian origin can also be used for this purpose. Transcription and translation control sequences for mammalian host cell expression vectors may be obtained from the viral genome. Promoter and enhancer sequences commonly used are derived from polyomavirus, adenovirus 2, etc. DNA sequences derived from the SV40 viral genome (e.g., SV40 origin, early and late promoters, enhancers, splice sites, polyadenylation sites) may also be used to provide other gene elements for expression of structural gene sequences in mammalian host cells. Vectors for use in mammalian host cells can be constructed, for example, by the method of Okayama and Berg (Mol. Cell. Biol., 3: 280, 1983, which is hereby incorporated by reference in its entirety).

One method of the present invention for producing a β-galactoside-α2,6-sialyltransferase protein comprises culturing host cells transformed with an expression vector carrying a nucleic acid sequence encoding a β-galactoside-α2,6-sialyltransferase protein, under conditions allowing expression of the protein. Then, in a manner suitable for the expression system used, the β-galactoside-α2,6-sialyltransferase protein is collected from the culture medium or cell extract.

Means for purifying a recombinant β-galactoside-α2,6-sialyltransferase protein are selected, as appropriate, depending on such factors as what type of host was used and whether the protein of the present invention is to be secreted into the culture medium. For example, means for purifying a recombinant β-galactoside-α2,6-sialyltransferase protein include column chromatography on an anion exchange column, a cation exchange column, a gel filtration column, a hydroxyapatite column, a CDP-hexanolamine agarose column, a CMP-hexanolamine agarose column and/or a hydrophobic column, as well as Native-PAGE or combinations thereof. Alternatively, when a recombinant β-galactoside-α2,6-sialyltransferase is expressed in a form fused with a tag or the like for easy purification, affinity chromatographic techniques may be used for purification. For example, when a histidine tag, a FLAG™ tag or glutathione-S-transferase (GST) is fused, purification can be accomplished by affinity chromatography using a Ni-NTA (nitrilotriacetic acid) column, an anti-FLAG antibody-bound column or a glutathione-bound column, respectively.

Although a recombinant β-galactoside-α2,6-sialyltransferase may be purified to give an electrophoretically single band, the β-galactoside-2,6-sialyltransferase of the present invention may be in either purified or partially purified form because it has sufficient activity even in partially purified form.

Antibody

The present invention provides an antibody against the β-galactoside-α2,6-sialyltransferase protein of the present invention. The antibody of the present invention may be prepared against the β-galactoside-α2,6-sialyltransferase protein of the present invention or a fragment thereof. A fragment of the β-galactoside-α2,6-sialyltransferase of the present invention used for this purpose is a fragment having a sequence comprising at least 6 amino acids, at least 10 amino acids, at least 20 amino acids or at least 30 amino acids of the amino acid sequence of the enzyme.

Such an antibody may be prepared by immunizing the β-galactoside-α2,6-sialyltransferase of the present invention or a fragment thereof into animals which are used for antibody preparation in the art including, but not limited to, mice, rats, rabbits, guinea pigs and goats. The antibody may be either polyclonal or monoclonal. The antibody can be prepared based on antibody preparation techniques well known to those skilled in the art.

The antibody of the present invention can be used for collecting the β-galactoside-α2,6-sialyltransferase protein of the present invention by affinity purification. The antibody of the present invention can also be used for detecting the β-galactoside-α2,6-sialyltransferase protein of the present invention in assays such as western blotting and ELISA.

Advantages of the Invention

By providing a novel β-galactoside-α2,6-sialyltransferase and a nucleic acid encoding the same, the present invention makes a contribution in terms of providing a means for synthesizing and producing sugar chains, which are now being shown to have important functions in the body. In particular, the β-galactoside-α2,6-sialyltransferase of the present invention has higher production efficiency and higher specific activity, as well as a wider range of acceptor substrate specificity, when compared to conventional sialyltransferases. Sialic acid is often located at the nonreducing termini of complex carbohydrate sugar chains in the body and is a very important sugar in terms of sugar chain functions. Thus, sialyltransferase is one of the most in demand enzymes among glycosyltransferases, and the provision of the novel sialyltransferase of the present invention meets such a high demand.

BRIEF DESCRIPTION OF DRAWINGS

FIG. 1-2 shows the results of HPLC analysis obtained for the reaction solution in which a crude enzyme solution from the strain JT-ISH-224 was reacted with pyridylaminated (PA) lactose. This figure shows the results of a control experiment relative to the experiment in FIG. 1-1, in which CMP-sialic acid was not mixed as a sialic acid donor into the reaction solution. The peak at a retention time of 3.993 minutes represents PA-lactose.

FIG. 1-3 shows the results of HPLC analysis obtained for a PA-lactose standard. PA-lactose appears as a peak at a retention time of 4.026 minutes.

FIG. 1-3 shows the results of HPLC analysis obtained for a PA-3'-sialyllactose standard. PA-3'-sialyllactose appears as a peak at a retention time of 5.447 minutes.

FIG. 1-5 shows the results of HPLC analysis obtained for the reaction solution in which a known β-galactoside-α2,6-sialyltransferase derived from *Photobacterium damselae* strain JT0160 was reacted with PA-lactose and CMP-sialic acid (i.e., pyridylaminated α2,6-sialyllactose was produced). The peaks at retention times of 4.000 and 4.406 minutes represent PA-lactose and PA-6'-sialyllactose, respectively.

FIG. 1-6 shows the results of HPLC analysis obtained for the reaction solution in which a known α2,6-sialyltransferase derived from *Photobacterium damselae* strain JT0160 was reacted with PA-lactose. This is a control experiment relative to the experiment in FIG. 1-5, in which CMP-sialic acid was not mixed into the reaction solution. The peak at a retention time of 3.995 minutes represents PA-lactose.

Figure 1:
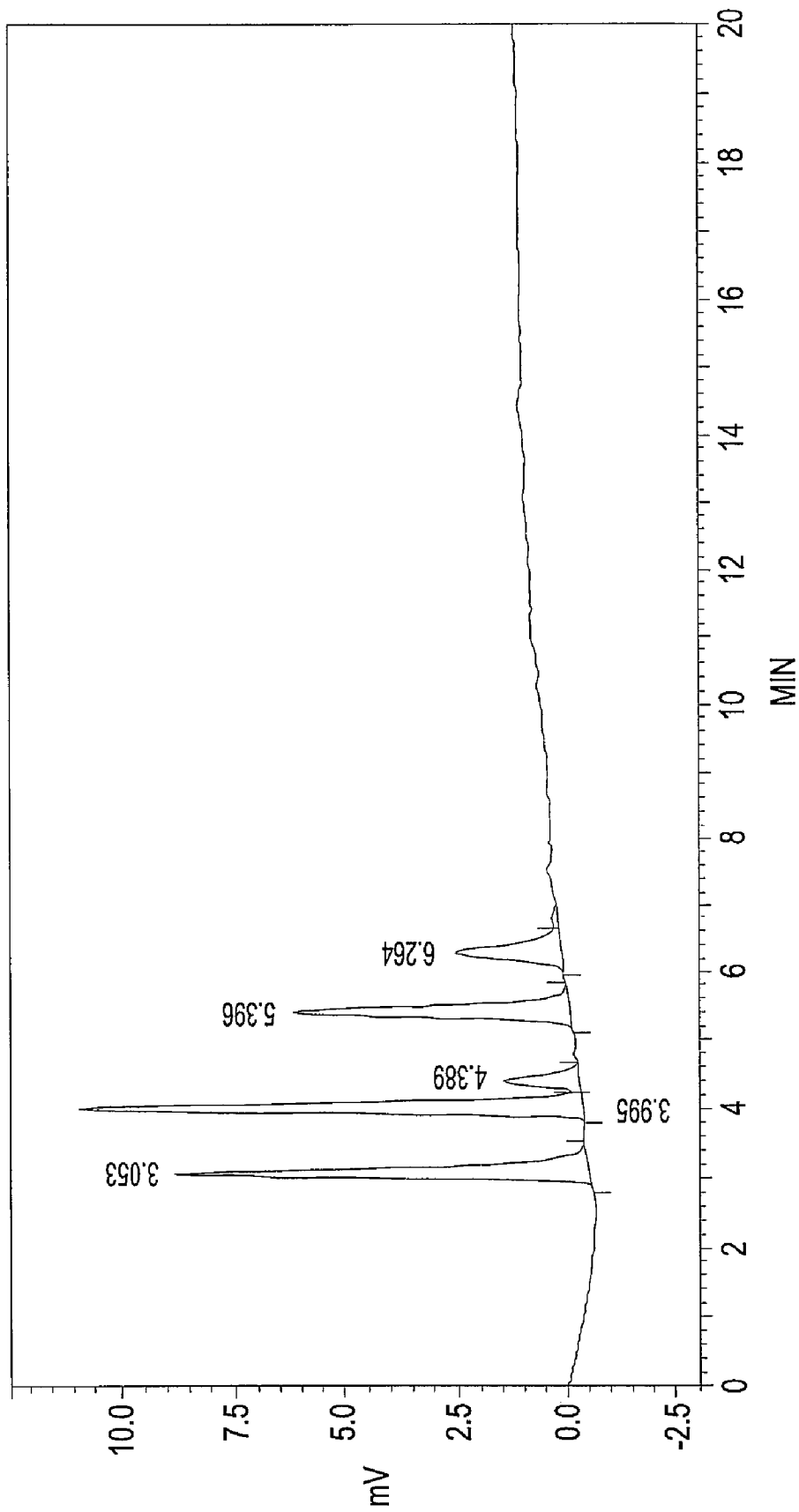
FIG. 1-1 shows the results of HPLC analysis obtained for the reaction solution in which a crude enzyme solution from the strain JT-ISH-224 was reacted with pyridylaminated lactose (PA-lactose) and CMP-sialic acid. The peaks at retention times of 3.995, 4.389 and 5.396 minutes represent PA-lactose, PA-6'-sialyllactose and PA-3'-sialyllactose, respectively.
Figures 1, 2:
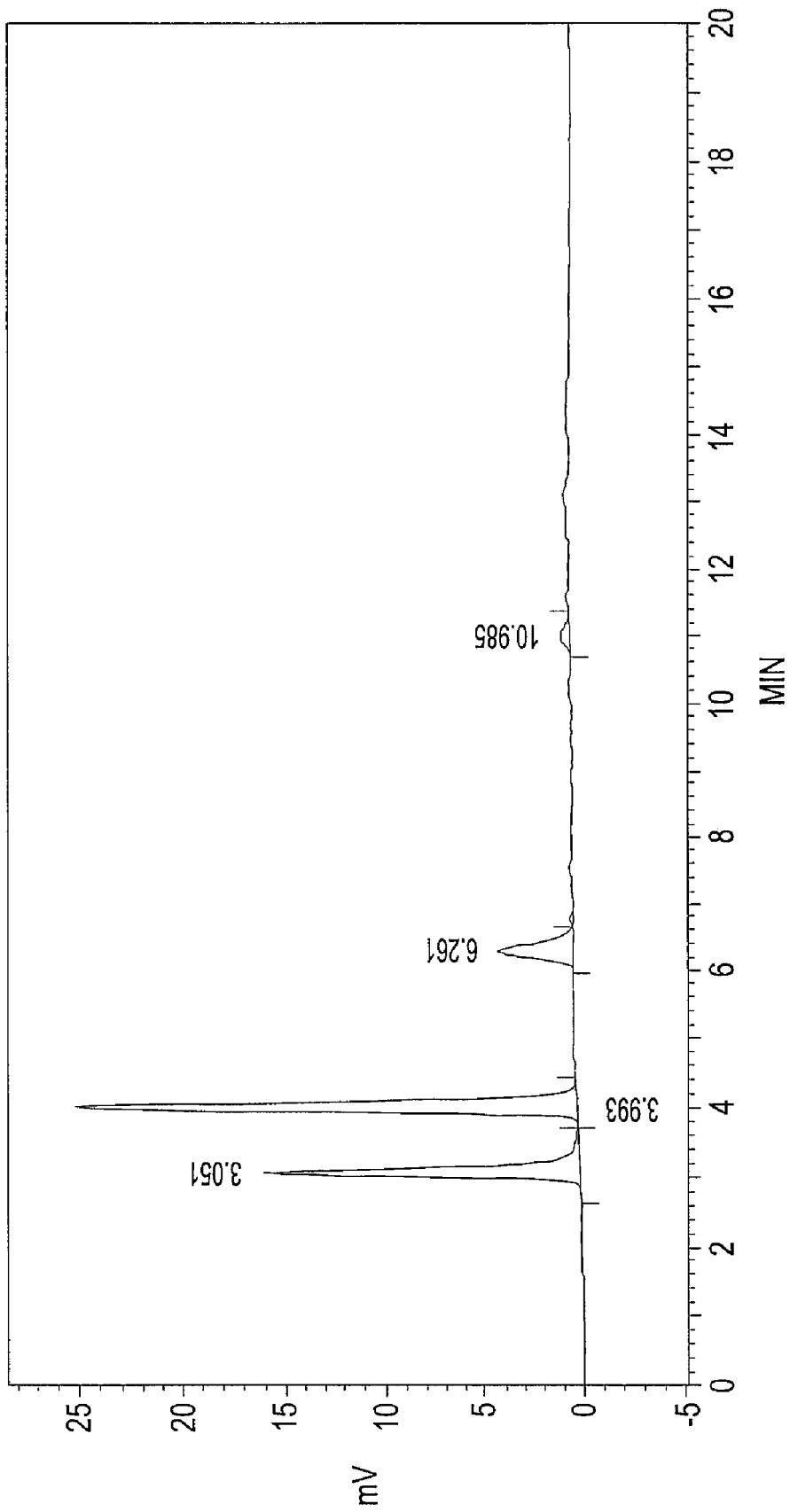

FIG. 2-1 is a graph showing the effect of reaction pH on the enzyme activity of JT-ISH-224-derived recombinant β-galactoside-α2,6-sialyltransferase N1C0. The abbreviations in the graph are as follows: Ac: acetate buffer, Cac: cacodylate buffer, Phos: phosphate buffer, and TAPS: TAPS buffer.

FIG. 2-2 is a graph showing the effect of reaction temperature on the enzyme activity of JT-ISH-224-derived recombinant β-galactoside-α2,6-sialyltransferase N1C0.

Figures 1, 2, 3:
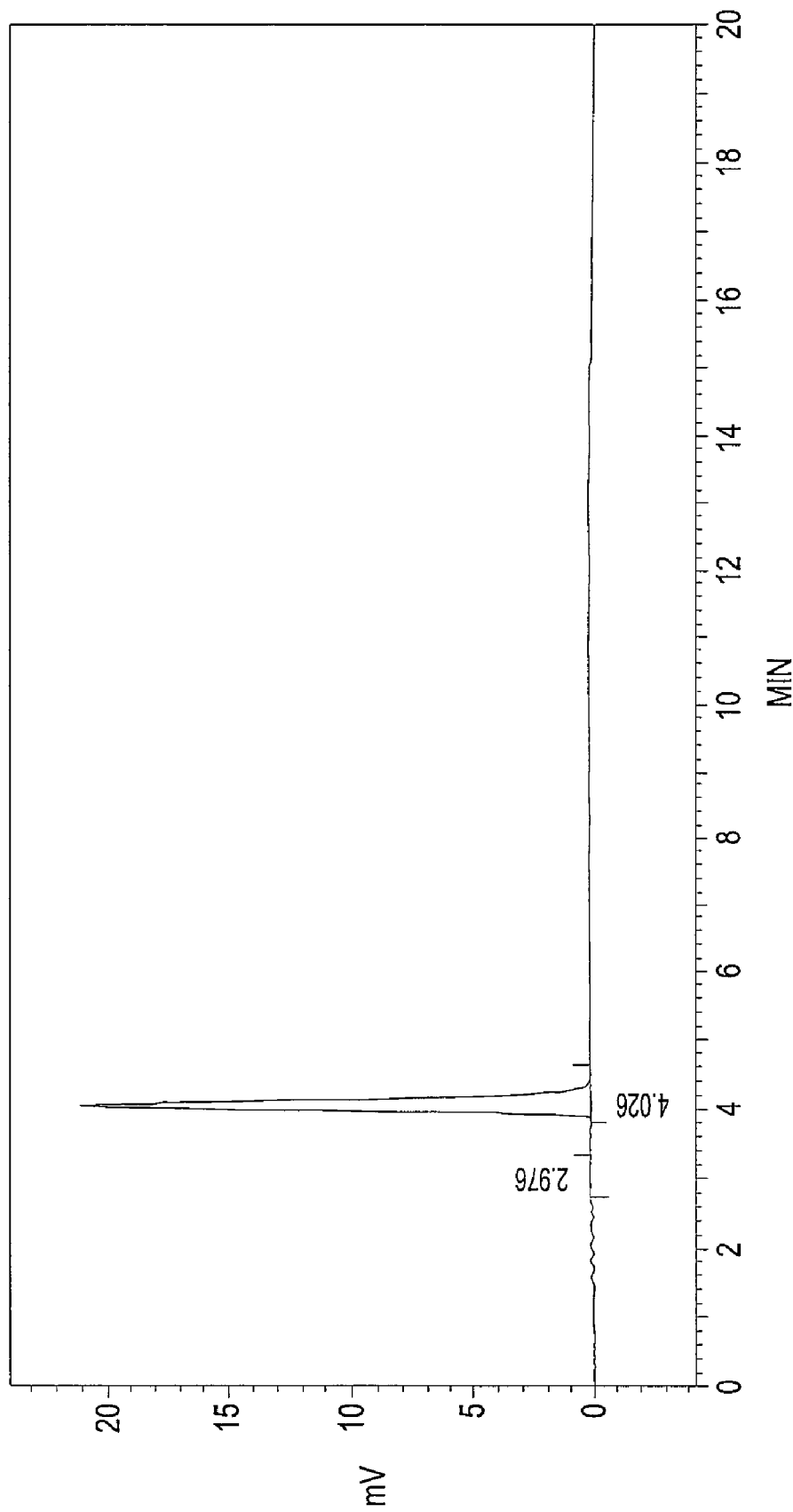
Figures 1, 2, 3, 4:
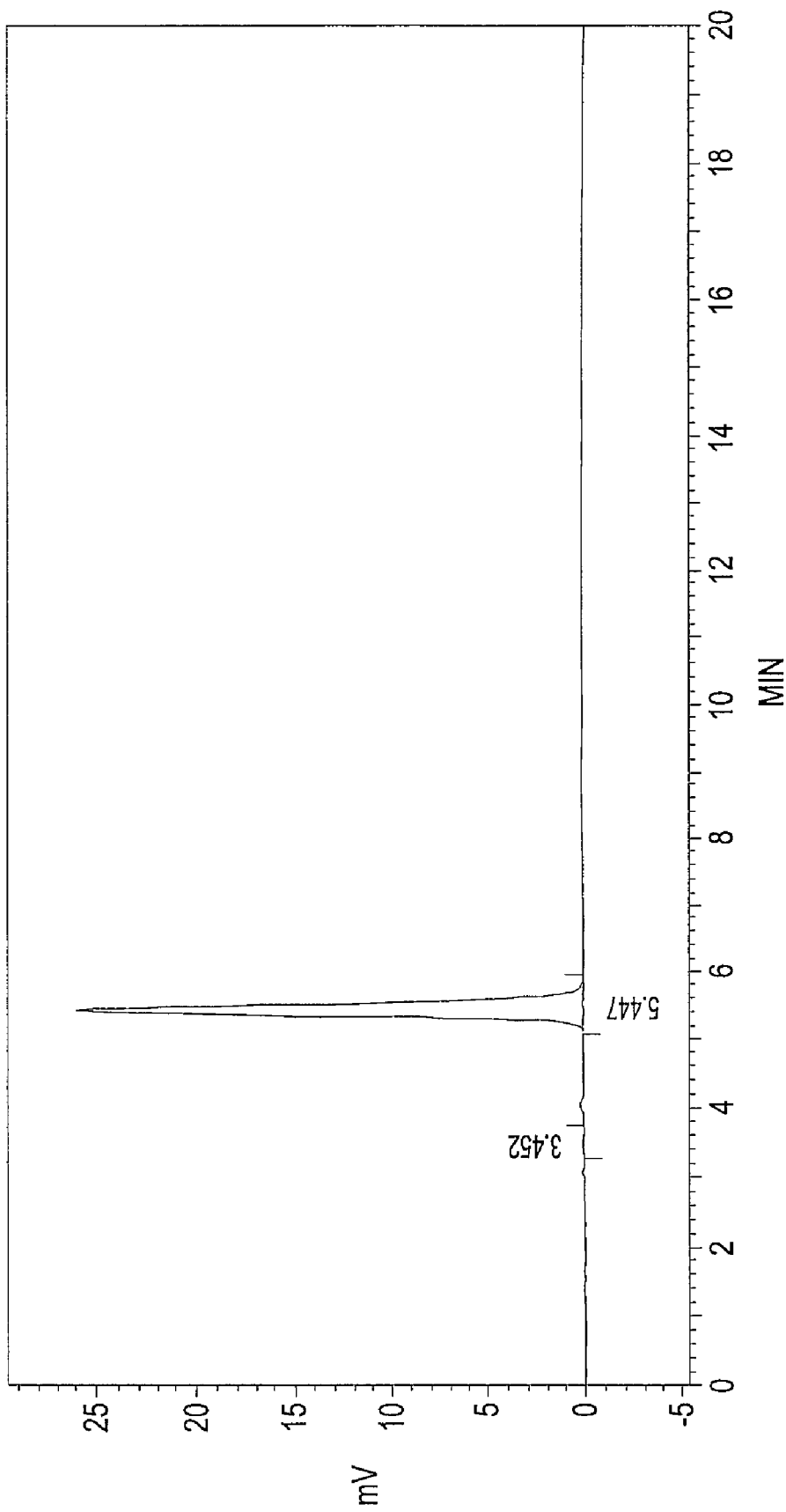
Figures 1, 2, 3, 4, 5:
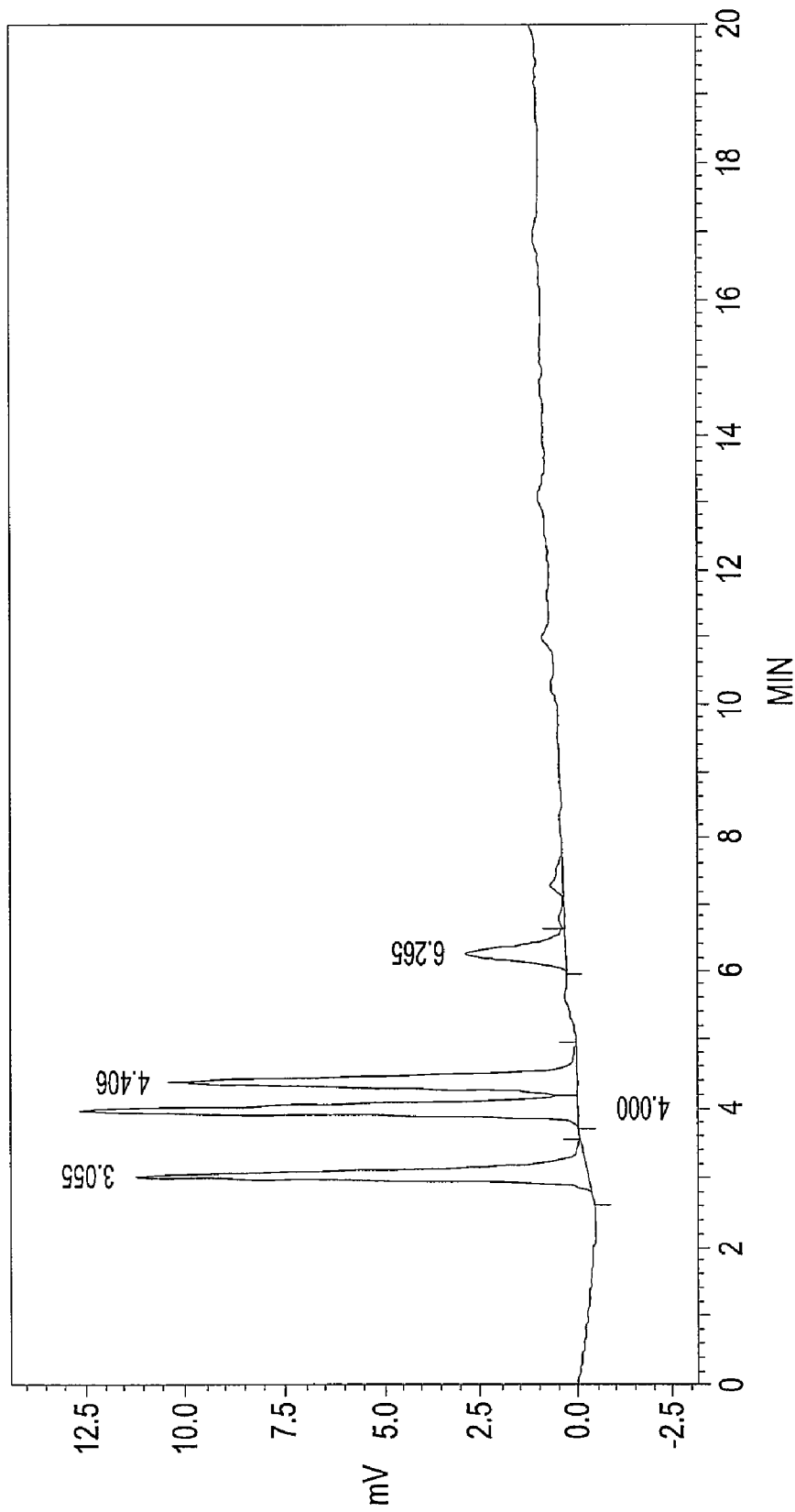
Figures 1, 2, 3, 4, 5, 6:
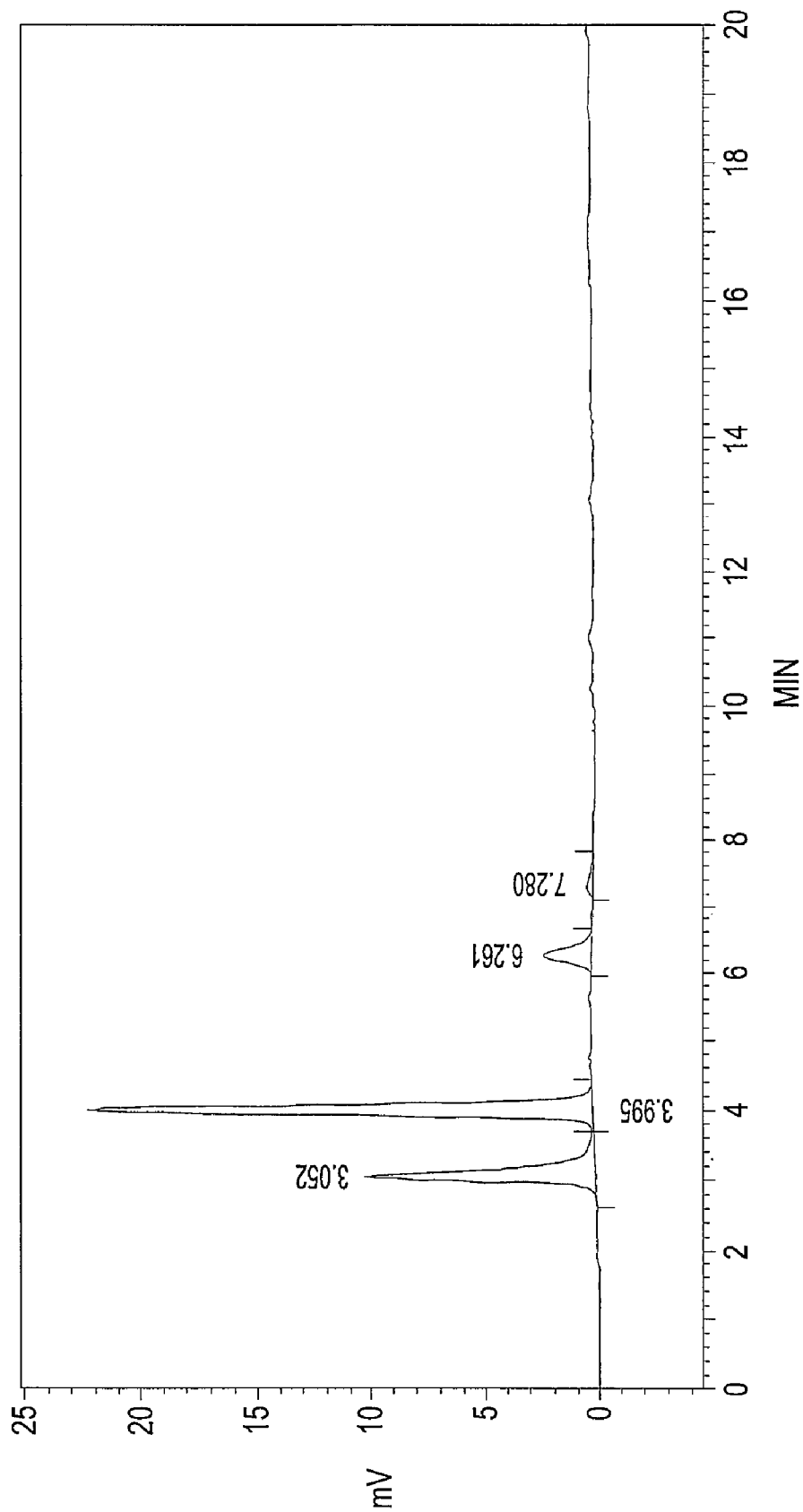
Figures 1, 2:
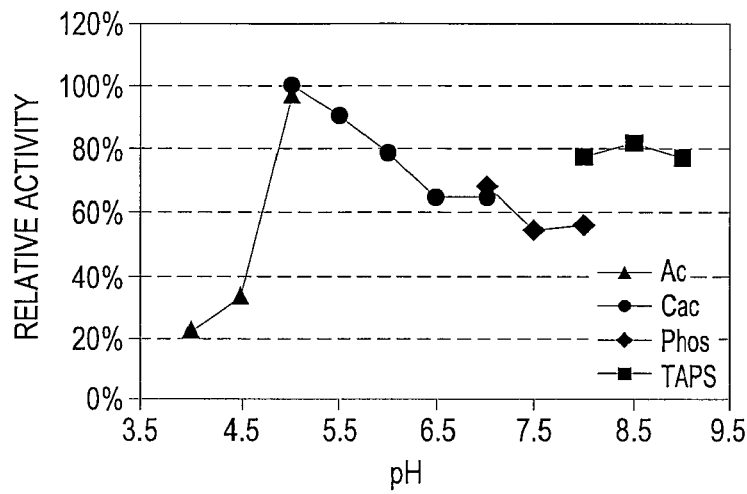
Figure 2:
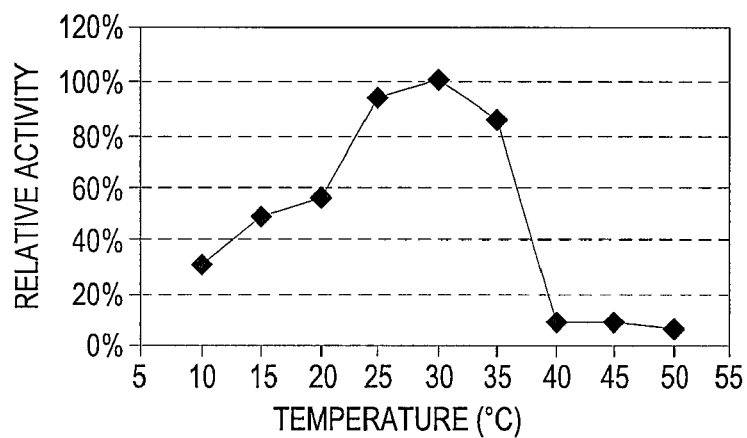
Figures 2, 3:
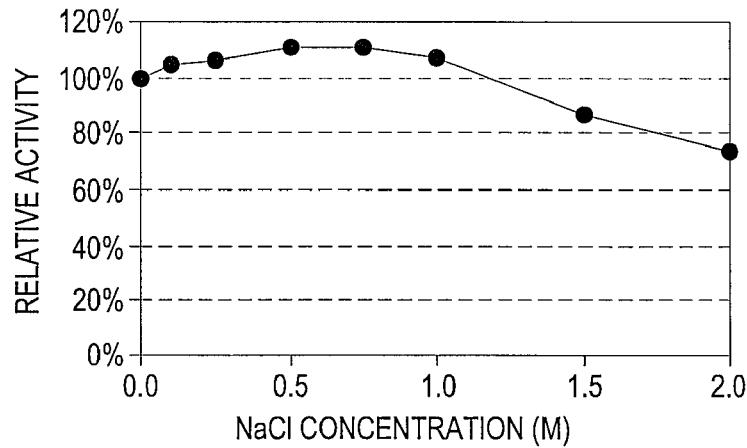

FIG. 2-3 is a graph showing the effect of NaCl concentration in the reaction solution on the enzyme activity of JT-ISH-224-derived recombinant β-galactoside-α2,6-sialyltransferase N1C0.

EXAMPLES

The present invention will now be described in more detail by way of the following examples, which are not intended to limit the technical scope of the invention. Based on the detailed description, modifications and changes will be apparent to those skilled in the art, and such modifications and changes fall within the technical scope of the invention.

Example 1

Screening and Strain Identification of Microorganisms Producing β-Galactoside-α2,6 Sialyltransferase Sea water, sea sand, sea mud or a marine product was used as an inoculum. This inoculum was applied onto agar plates containing marine broth agar 2216 medium (Becton Dickinson) to obtain microorganisms growing at 15° C., 25° C. or 30° C. After the resulting microorganisms were pure-cultured in a routine manner, each microorganism was cultured using a liquid medium composed of marine broth 2216 medium (Becton Dickinson). After the microorganisms were fully grown, the cells were collected from each culture solution by centrifugation. To the collected cells, 20 mM cacodylate buffer (pH 6.0) containing 0.2% Triton® X-100 (Kanto Kagaku, Japan) was added, and the cells were suspended therein. This cell suspension was ultrasonicated under ice cooling to homogenize the cells. This cell homogenate was used as a crude enzyme solution and measured for its sialyltransferase activity, thus obtaining a strain having sialyltransferase activity, i.e., JT-ISH-224. Incidentally, the strain JT-ISH-224 was obtained from the internal organs of barracuda.

Sialyltransferase activity was measured as described in J. Biochem., 120, 104-110 (1996) (which is hereby incorporated by reference in its entirety). More specifically, the enzymatic reaction was accomplished by using CMP-NeuAc (70 nmol, containing about 20,000 cpm CMP-NeuAc in which NeuAc was labeled with $^{14}C$; NeuAc represents N-acetylneuraminic acid) as a glycosyl donor substrate, lactose (1.25 μmol) as a glycosyl acceptor substrate, NaCl added to give a concentration of 0.5 M, and the enzyme-containing reaction solution (30 μl) prepared as described above. The enzymatic reaction was carried out at 25° C. for about 10 to 180 minutes. After completion of the reaction, 1.97 ml of 5 mM phosphate buffer (pH 6.8) was added to the reaction solution, which was then applied to a Dowex 1×8 ($PO_4^{3-}$ form, 0.2×2 cm, BIO-RAD) column. The radioactivity was measured for the reaction product, i.e., sialyllactose contained in the eluate (0 to 2 ml) from this column to calculate the enzyme activity. One enzyme unit (1 U) is defined as the amount of enzyme required to transfer 1 micromole of sialic acid per minute.

To determine the binding mode of sialic acid, a reaction using PA-lactose as a substrate was then performed. The enzymatic reaction was accomplished by using the resulting crude enzyme solution and a pyridylaminated sugar chain as a glycosyl acceptor substrate. The pyridylaminated sugar chain used for analysis was pyridylaminated lactose (Galβ1-4Glc-PA, Takara Bio Inc., Japan). To 5 μl of the crude enzyme solution, 1.5 μl of 5 mM CMP-NeuAc and 1.5 μl of 10 pmol/μl glycosyl acceptor substrate were added and reacted at 25° C. for 18 hours. After the reaction, the reaction solution was treated at 100° C. for 2 minutes to inactivate the enzyme, followed by HPLC to analyze the reaction product. The HPLC system used was Shimadzu LC10A (Shimadzu Corporation, Japan) and the analytical column used was Takara PALPAK Type R (Takara Bio Inc., Japan). The column which had been equilibrated with 100 mM acetate-triethylamine (pH 5.0) containing 0.15% N-butanol was injected with the reaction solution supplemented with 72 μl of Eluent A (100 mM acetate-triethylamine, pH 5.0). For elution of pyridylaminated sugar chains, Eluent A (100 mM acetate-triethylamine, pH 5.0) and Eluent B (100 mM acetate-triethylamine containing 0.5% n-butanol, pH 5.0) were used to successively elute the pyridylaminated sugar chains with a linear gradient of 30% to 50% Eluent B (0 to 20 minutes) and then 100% Eluent B (21 to 35 minutes). The analysis was performed under the following conditions: flow rate: 1 ml/min, column temperature: 40° C., detection: fluorescence (Ex: 320 nm, Em: 400 nm). The results indicated that the strain JT-ISH-224 had both β-galactoside-α2,6-sialyltransferase activity and β-galactoside-α2,3-sialyltransferase activity (FIGS. 1-1 to 1-6).

Bacteriological Identification of Strain JT-ISH-224

The resulting strain JT-ISH-224 was found to have the following properties:
(Microbiological Properties)
(1) The cells are in bacillary form and have a size of 0.7 to 0.8 μm×1.0 to 1.5 μm.
(2) Motility: +
(3) Gram staining: −
(4) Spore: −
(Physiological and Biochemical Properties)
(1) Growth temperature: − at 4° C., + at 25° C., + at 30° C., − at 37° C.
(2) Colony color: not producing characteristic colony pigment
(3) O/F test: +/−
(4) Catalase test: +
(5) Oxidase test: +
(6) Acid production from glucose: +
(7) Gas generation from glucose: +
(8) Photogenesis: −
(9) Reduction of nitrate: +
(10) Indole formation: +
(11) Glucose acidification: −
(12) Arginine dihydrolase: +
(13) Urease: −
(14) Esculin hydrolysis: −
(15) Gelatin hydrolysis: −

(16) β-Galactosidase: +
(17) Glucose assimilation: −
(18) L-Arabinose assimilation: −
(19) D-Mannose assimilation: −
(20) D-Mannitol assimilation: −
(21) N-Acetyl-D-glucosamine assimilation: −
(22) Maltose assimilation: −
(23) Potassium gluconate assimilation: −
(24) n-Capric acid assimilation: −
(25) Adipic acid assimilation: −
(26) dl-Malic acid assimilation: −
(27) Sodium citrate assimilation: −
(28) Phenyl acetate assimilation: −
(29) Cytochrome oxidase: +
(30) O/129 sensitivity: 10 μg−, 15 μg+
(31) GC content of DNA isolated from bacterial cells (mol %): 39.4%

Nucleotide Sequence Analysis of 16S rRNA Gene

The genomic DNA extracted from the strain JT-ISH-224 in a routine manner was used as a template for PCR to amplify the entire nucleotide sequence of the 16S rRNA gene, thereby determining its nucleotide sequence. The nucleotide sequence is shown in SEQ ID NO: 5.

The strain JT-ISH-224 was shown to belong to the Vibrionaceae, based on its morphological observations including growth on marine agar, bacillary form, Gram staining, fermentative glucose degradation and O/129 sensitivity, along with the results from the physiological and biochemical property tests. Moreover, the DNA nucleotide sequence of the 16S rRNA gene in the strain JT-ISH-224 was found to share the highest homology (99.2%) with the sequence of the 16S rRNA gene in *Photobacterium phosphoreum* the type strain ATCC11040, and the second highest homology (99.1%) with the sequence of the 16S rRNA gene in *Photobacterium iliopiscarium* the type strain ATCC51760. These results indicated that the strain JT-ISH-224 is a microorganism belonging to the genus *Photobacterium* of the family Vibrionaceae (*Photobacterium* sp.).

Example 2

Cloning and Nucleotide Sequencing of β-galactoside-α2,6-sialyltransferase Gene from Strain JT-ISH-224, and *E. coli* Expression of the Gene (1) Confirmation of the Presence of β-galactoside-α2,6-sialyltransferase Gene Homologue in Strain JT-ISH-224

To determine whether there was a homologue of the β-galactoside-α2,6-sialyltransferase gene derived from *Photobacterium damselae* strain JT0160, genomic Southern hybridization was performed on the strain JT-ISH-224 that was found to have β-galactoside-α2,6-sialyltransferase activity in Example 1. From a cell pellet of the strain JT-ISH-224 (about 0.5 g), genomic DNA (about 100 μg) was prepared using a Qiagen Genomic-tip 100/G (Qiagen) in accordance with the instructions attached to the kit. The genomic DNA (several micrograms) from the strain JT-ISH-224 was then digested with a restriction enzyme EcoRI or HindIII and fractionated by 0.7% agarose gel electrophoresis, followed by alkaline blotting with 0.4 M NaOH to transfer the gel onto a Hybond-N+ nylon membrane filter (Amersham Biosciences). Southern hybridization was performed on this filter using as a probe a partial fragment (i.e., an EcoRI-HindIII fragment of approximately 1.2 kb covering ATG to HindIII) of the β-galactoside-α2,6-sialyltransferase gene from *Photobacterium damselae* strain JT0160 (GeneBank Accession No. E17028). The hybridization experiment was performed using an ECL direct labelling & detection system (Amersham). The probe was labeled according to the instructions attached to the kit. Hybridization was accomplished at 37° C. (generally at 42° C.) for 4 hours using the hybridization buffer included in the kit, which was supplemented with 5% (w/v) Blocking reagent and 0.5 M NaCl. Washing was performed twice in 0.4% SDS, 0.5×SSC at 50° C. (generally 55° C.) for 20 minutes and once in 2×SSC at room temperature for 5 minutes. Signal detection was performed according to the instructions attached to the kit. As a result, EcoRI digestion detected a band of approximately 12.5 kb, while HindIII digestion detected a band of approximately 9 kb. These results indicated that the strain JT-ISH-224 had a homologue of the β-galactoside-α2,6-sialyltransferase gene from *Photobacterium damselae* strain JT0160.

(2) Cloning of β-galactoside-α2,6-sialyltransferase Gene from Strain JT-ISH-224

(i) Construction of Genomic Library

Relative to 1-2 μg of the genomic DNA from the strain JT-ISH-224, 0.1 to 0.2 units of Sau3AI, a four base-cutter enzyme, was used for partial digestion of the DNA. The genomic DNA was treated in a total amount of 80 μg. The reaction buffer used was one attached to the enzyme and the reaction conditions were set at 37° C. for 30 minutes. After the reaction, EDTA (pH 8.0) was added at a final concentration of 25 mM to the reaction solution, followed by phenol/chloroform treatment. The genomic DNA was collected by ethanol precipitation and dissolved in 400 μl TE. In a centrifugal tube (Hitachi 40PA), a 40-10% gradient was prepared from 40% sucrose buffer (20 mM Tris pH 8.0, 5 mM EDTA pH 8.0, 1 M NaCl) and 10% sucrose buffer using a gradient preparation unit, and the above partially-digested DNA solution was overlayed thereon. Using an ultracentrifuge (Hitachi SCP70H, rotor: SRP28SA), the tube was centrifuged at 26,000 rpm at 20° C. for 15 hours. After centrifugation, a hole was made with a 25G needle at the bottom of the tube to collect every 1 ml aliquots from the solution at the bottom. Using a submarine electrophoretic chamber, a part of each collected sample containing the genomic DNA was electrophoresed on a 0.5-0.6% agarose gel/TAE buffer at 26 V for 20 hours to observe a fraction containing DNA of 9-16 kb size. As a marker, λ/HindIII was used. After addition of 2.5 ml TE to reduce the sucrose concentration, the fraction containing the DNA fragment of 9-16 kb size was ethanol precipitated, rinsed and dissolved in a small volume of TE.

λDASH II (Stratagene) was used as a vector to create a genomic library of the strain JT-ISH-224. The λDASH II/BamHI vector and the genomic DNA fragment were ligated overnight at 12° C. using a Stratagene ligation kit. After the reaction, the reaction solution was reacted with GIGAPACK® III Gold Packaging extract, whereby the λ vector carrying the genomic DNA was incorporated into phage particles. The phage solution was stored at 4° C. in 500 μl SM buffer and 20 μl chloroform. *E. coli* XL1-Blue MRA (P2) (Stratagene) was grown in LBMM (LB+0.2% maltose+10 mM MgSO$_4$) to A$_{600}$=0.5, and 200 μl of this culture solution was incubated with an appropriate amount of the phage solution at 37° C. for 15 minutes. This solution was mixed with 4 ml NZY top agarose kept at 48° C., and plated in a NZY agar plate (a plastic dish of 9 cm diameter). The plate was cultured overnight at 37° C. and the number of plaques was counted to calculate the titer. As a result, the library size was calculated to be about 300,000 pfu (plaque forming unit).

Next, the above-mentioned partial fragment of the β-galactoside-α2,6-sialyltransferase gene from *Photobacterium* damselae strain JT0160 was used as a probe to screen the genomic library of the strain JT-ISH-224. In a round dish of 9 cm diameter, several hundred pfu of phages were plated together with XL1-blue MRA(P2) host cells according to the instructions attached to a λDASH II/BamHI vector kit (Stratagene). Plaques were contacted with a HYBOND™ N+ nylon membrane filter (Amersham), treated with alkali according to the instructions attached to the membrane to cause DNA denaturation, and then fixed on the membrane. Probe labeling and hybridization conditions are as described in (1) above. As a result, 8 clones were obtained up to the end of secondary screening (also serving as plaque purification), 4 of which were collected and each was plated in a NZY plate together with *E. coli* XL1-blue MRA(P2) at several ten thousand pfu per plate and incubated overnight at 37° C. SM buffer was added in 4 ml volumes to 6 plates with confluent plaques, and the plates were allowed to stand overnight at 4° C. Phage plate lysates were collected with Pasteur pipettes, and λ DNA was extracted and purified from each lysate with a QIAGEN® Lambda Mini Kit (QIAGEN). These 4 λDNA samples were digested with restriction enzymes EcoRI & HindIII, EcoRI & BamHI, or EcoRI & XhoI. Each digest was fractionated by agarose gel electrophoresis and transferred onto a nylon membrane filter, as described in (1) above. This filter was provided for Southern analysis using as a probe the partial fragment of the β-galactoside-α2,6-sialyltransferase gene from *Photobacterium damselae* strain JT0160. As a result, EcoRI-BamHI digestion detected a band of 10 kb. Since a genome of 10 kb in length appeared difficult to be subcloned into a high-copy plasmid vector in a routine manner, Southern hybridization was further performed with various restriction enzymes. The enzymes used were BglII, EcoRV, KpnI, NheI, PstI, PvuII, SacI, SalI and XbaI. As a result, EcoRV digestion detected a band of 6.6 kb, KpnI digestion detected a band of 7 kb, and NheI digestion detected a band of 3.5 kb. Then, each λDNA sample was digested again with NHeI, followed by agarose gel electrophoresis in TAE buffer using a low melting point agarose (SEAPLAQUE® GTG®). A DNA fragment of 3.5 kb was excised as a gel piece, supplemented with an equal volume of 200 mM NaCl and treated at 65° C. for 10 minutes to dissolve the gel. This sample was extracted once with phenol, once with phenol/chloroform, and then once with chloroform, followed by ethanol precipitation to collect the 3.5 kb DNA fragment. This fragment was ligated with a Ligation kit (Takara Bio Inc., Japan) to a XbaI site of plasmid vector pBLUESCRIPT® SK(−) which had been dephosphorylated. After ligation, the DNA was transformed into *E. coli* TB1 by electroporation and plated onto LA agar medium containing ampicillin (100 μg/mL). After culturing overnight at 37° C., the resulting multiple colonies were inoculated into LB medium (containing ampicillin) and cultured overnight with shaking at 37° C., followed by plasmid extraction in a routine manner (Sambrook et al. 1989, Molecular Cloning, A laboratory manual, $2^{nd}$ edition (hereby incorporated by reference in its entirety)).

(iii) Determination of the Entire Nucleotide Sequence of β-Galactoside-α2,6-Sialyltransferase Gene from Strain JT-ISH-224

Next, nucleotide sequences at both ends of the 3.5 kb NheI fragment were determined for the plasmid confirmed above to carry the insert DNA by using M13 primers (Takara Bio Inc., Japan) in an ABI PRISM® fluorescent sequencer (Model 310 Genetic Analyzer, Perkin Elmer). The resulting DNA sequences were translated into amino acid sequences using genetic information processing software GENETYX Ver.7 (Genetyx Corporation, Japan), and an identity search with the BLAST program was made for these amino acid sequences against the GeneBank database of the National Center for Biotechnology Information (NCBI). As a result, the amino acid sequence translated from one of the DNA sequences showed significant identity with the amino acid sequence of β-galactoside-α2,6-sialyltransferase derived from *Photobacterium damselae* strain JT0160. The orientation of the region showing identity suggested that the 3.5 kb NheI fragment contained the entire β-galactoside-α2,6-sialyltransferase gene from the strain JT-ISH-224.

Next, to determined the entire DNA sequence of this enzyme gene from the strain JT-ISH-224, the following two primers were synthesized based on the DNA sequence obtained from the 3.5 kb NheI fragment, and used for nucleotide sequencing:

```
ISH224-26ST-C3-R
(5'-TTCATCGTCATCTAATCGTGGC-3'  (22 mer): SEQ ID
NO: 6);
and ISH224-26ST-C4-R
(5'-AGTTGTTGCGTACCACAAGT-3'  (20 mer): SEQ ID
NO: 7).
```

Using these primers, nucleotide sequencing was performed as described above. As a result, the sequence of SEQ ID NO: 1 in the Sequence Listing was obtained. This sequence corresponds to the entire nucleotide sequence of the open reading frame (ORF) of the β-galactoside-α2,6-sialyltransferase gene from the strain JT-ISH-224. The ORF of the β-galactoside-α2,6-sialyltransferase gene from *Photobacterium* sp. strain JT-ISH-224 was composed of 1545 base pairs and encoded 514 amino acids. This amino acid sequence is shown in SEQ ID NO: 2 in the Sequence Listing. Upon analysis of DNA and amino acid sequences using GENETYX Ver.7, the DNA sequence of the β-galactoside-α2,6-sialyltransferase gene from the strain JT-ISH-224 was found to share an identity of 63% with the β-galactoside-α2,6-sialyltransferase gene from *Photobacterium damselae* strain JT0160. Likewise, its amino acid sequence was found to share an identity of 54.5% with β-galactoside-α2,6-sialyltransferase (JC5898) from *Photobacterium damselae* strain JT0160.

(3) Construction of Expression Vector for β-galactoside-α2, 6-sialyltransferase Gene from Strain JT-ISH-224

To test whether the cloned gene had sialyltransferase activity or to obtain β-galactoside-α2,6-sialyltransferase derived from the strain JT-ISH-224 in large amounts, the full length of the gene and its derivative modified to remove the N-terminal signal peptide region were each integrated into an expression vector to produce a protein in *E. coli* cells, followed by measuring the activity of this expressed protein.

Genetic information processing software GENETYX Ver.7 was used to analyze the amino acid sequence of β-galactoside-α2,6-sialyltransferase derived from the strain JT-ISH-224, estimating that the N-terminal 17 amino acids would constitute the signal peptide. Then, primers for cloning the full-length gene (herein referred to as "ISH224-N0C0"): ISH224-26ST-N0BspHI (5'-AGAATATCATGAAAAACTTTTTATTATTAAC-3' (31 mer): SEQ ID NO: 8) and ISH224-26ST-C0BamHI (5'-TTTTTTGGATCCCTAGACTGCAATACAAACACC-3' (33 mer): SEQ ID NO: 10), as well as primers for cloning a gene encoding a protein lacking the amino acids of the signal peptide region (herein referred to as "ISH224-N1C0"): ISH224-26ST-N1PciI (5'-CTTGTAACATGTCAGAAGAAAATACACAATC-3' (31 mer): SEQ ID NO: 9) and ISH224-26ST-C0BamHI (5'-

TTTTTTGGATCCCTAGACTGCAATACAAACACC-3' (33 mer): SEQ ID NO: 10) were designed and synthesized.

PCR was carried out with these primers using the plasmid carrying the 3.5 kb NheI fragment as a template to amplify the β-galactoside-α2,6-sialyltransferase gene from the strain JT-ISH-224 for use in integration into an expression vector. The reaction conditions for PCR were set as follows. In 50 µl reaction solution containing 500 ng template DNA, 5 µl 10×EX TAQ™ buffer, 4 µl 2.5 mM dNTPs, 50 pmol primer and 0.5 µl EX TAQ™ (Takara Bio Inc., Japan), PCR was carried out using a Program Temp Control System PC-700 (ASTEK) under the following conditions: 96° C. for 3 minutes, (96° C. for 1 minute, 55° C. for 1 minute, 72° C. for 2 minutes)×5 cycles, and 72° C. for 6 minutes. As a result, PCR products of approximately 1.55 kb and 1.5 kb were amplified for ISH224-N0C0 and ISH224-N1C0 respectively. These PCR products were each cloned into vector pCR4TOPO (Invitrogen). Ligation was carried out according to the instructions attached to the vector kit. Each DNA was introduced into E. coli TB1 by electroporation and the plasmid DNA was extracted in a routine manner (Sambrook et al. 1989, Molecular Cloning, A laboratory manual, $2^{nd}$ edition). Clones confirmed to have the insert were each analyzed by PCR with M13 primers (Takara Bio Inc., Japan) to determine the nucleotide sequence of the PCR product from both ends using an ABI PRISM® fluorescent sequencer (Model 310 Genetic Analyzer, Perkin Elmer). As a result, ISH224-N0C0 had a nucleotide substitution from thymine (T) to cytosine (C) at position 718 of SEQ ID NO: 1 in the Sequence Listing. This mutation results in a codon change from TTA to CTA, but causes no amino acid mutation because these codons both encode leucine (Leu). On the other hand, ISH224-N1C0 had no mutation in its nucleotide sequence. The nucleotide sequence of ISH224-N1C0 is shown in SEQ ID NO: 3.

One selected clone of ISH224-N0C0 or ISH224-N1C0 whose nucleotide sequence was confirmed was double-digested with restriction enzymes BspHI & BamHI (for ISH224-N0C0) or PciI & BamHI (for ISH224-N1C0), followed by gel purification as described in (2)(ii) above. pTrc99A (Pharmacia LKB) was used as a vector for E. coli expression. After being double-digested with restriction enzymes NcoI & BamHI and purified on a gel, this vector was ligated with the restriction enzyme-treated PCR product of ISH224-N0C0 or ISH224-N1C0 using a Takara Ligation Kit (Takara Bio Inc., Japan) and transfected into E. coli TB1. In a routine manner, the plasmid DNA was extracted and analyzed by restriction enzyme analysis to confirm the integration of the insert, thereby completing ISH224-N0C0/pTrc or ISH224-N1C0/pTrc.

Further, to create various truncated proteins of β-galactoside-α2,6-sialyltransferase derived from the strain JT-ISH-224, the following primers were designed.

Primer Name, Sequence (SEQ ID NO), Length

```
224-26-N2Bsp
                                         (SEQ ID NO: 15)
AAACTTTCATGACGCAACAACTATTAACAGAA, 32 mer 224-26-N3Bsp
                                         (SEQ ID NO: 16)
AAGTAATCATGAACGTAGTGGCTCCATCTTTA, 32 mer 224-26-N3.1Bsp
                                         (SEQ ID NO: 17)
CACGTGTCATGACTCTTCAGCAGCTAATGGAT, 32 mer
```

224-26-N2Bsp allows deletion of N-terminal 62 amino acids and introduction of methionine at the N-terminus. 224-26-N3Bsp allows deletion of N-terminal 110 amino acids and introduction of methionine at the N-terminus. 224-26-N3.1Bsp allows deletion of N-terminal 127 amino acids and introduction of methionine at the N-terminus. Using these primers in combination with primer ISH224-26ST-C0BamHI shown above, PCR was carried out as described above using ISH224-N1C0 as a template. The resulting PCR products were each cloned into vector pCR4TOPO (Invitrogen) and confirmed for their nucleotide sequence. As a result, in all clones obtained with these primer combinations, their nucleotide sequences were found to share 100% homology with the nucleotide sequence of ISH224-N1C0 used as a template. The clone obtained from a combination of 224-26-N2Bsp and ISH224-26ST-C0BamHI was designated as N2C0. Likewise, the clone obtained from a combination of 224-26-N3Bsp and ISH224-26ST-C0BamHI was designated as N3C0, while the clone obtained from a combination of 224-26-N3.1Bsp and ISH224-26ST-C0BamHI was designated as N3.1C0. After being double-digested with restriction enzymes BspHI & BamHI, these clones were each cloned into an E. coli expression vector (pTrc99A) as described above to thereby complete ISH224-N2C0/pTrc, ISH224-N3C0/pTrc and ISH224-N3.1;C0/pTrc.

(4) Expression Induction and Activity Measurement

An induction experiment of protein expression was performed on the five clones obtained in (3) above (i.e., ISH224-N0C0/pTrc, ISH224-N1C0/pTrc, ISH224-N2C0/pTrc, ISH224-N3C0/pTrc and ISH224-N3.1C0/pTrc). A single colony of E. coli TB1 having the expression vector pTrc99A carrying each clone was inoculated into LB medium (6 ml) containing an antibiotic, ampicillin (final concentration 100 µg/mL), and pre-cultured at 30° C. to about $A_{600}$=0.5, followed by addition of IPTG (isopropyl-β-D(−)-thiogalactopyranoside, Wako Pure Chemical Industries, Ltd., Japan) at a final concentration of 1 mM. After culturing with shaking at 30° C. for an additional 4 hours, the cells in 4 ml culture solution were collected by centrifugation. These cells were suspended in 200 µl of 20 mM Bis-Tris buffer (pH 7.0) containing 0.336% Triton® X-100 and 0.5 M sodium chloride, and ultrasonically homogenized under ice cooling. The resulting homogenate was defined as a crude enzyme solution, diluted 200-fold with 20 mM cacodylate buffer (pH 5.0) containing 0.336% Triton® X-100, and then provided for activity measurement. The reaction was carried out in duplicate. The reaction conditions are as indicated in the footnotes of Tables 1-1 and 1-2. As a result, as shown in Tables 1-1 and 1-2 below, it was demonstrated that there was a factor transferring $^{14}$C-labeled NeuAc in the glycosyl donor CMP-NeuAc to the glycosyl acceptor substrate lactose, i.e., sialyltransferase activity in the crude enzyme solutions from all clones but ISH224-N3.1C0/pTrc. These results indicated that E. coli cells into which ISH224-N0C0/pTrc, ISH224-N1C0/pTrc, ISH224-N2C0/pTrc or ISH224-N3C0/pTrc had been introduced expressed sialyltransferase.

In view of the foregoing, ISH224-N3C0 was found to be the smallest clone that retained the activity of β-galactoside-α2,6-sialyltransferase derived from the strain JT-ISH-224. Thus, it was indicated that the presence of at least amino acids 111-514 of SEQ ID NO: 2 allowed retention of β-galactoside-α2,6-sialyltransferase activity.

TABLE 1-1

Sialyltransferase activity in homogenate of E. coli into which β-galactoside-α2,6-sialyltransferase gene from strain JT-ISH-224 is introduced

| Crude enzyme solution | Radioactivity (cpm) | | |
|---|---|---|---|
| | Round 1 | Round 2 | Average |
| ISH224-N0C0 clone | 2859 | 2617 | 2738 |
| ISH224-N1C0 clone | 1552 | 1711 | 1631.5 |
| Absence | 94 | 113 | 103.5 |

Reaction Conditions
Reaction composition:

| | |
|---|---|
| 3 M NaCl | 5 μl |
| 45 mg/ml Lactose (in 20 mM cacodylate buffer (pH 5)) | 10 μl |
| Crude enzyme solution diluted 200-fold | 5 μl |
| 4.55 mM CMP-sialic acid (in 20 mM cacodylate buffer (pH 5)) + $^{14}$C-CMP-sialic acid | 5 μl |

Reaction time: 2 minutes
Reaction temperature: 30° C.

TABLE 1-2

Sialyltransferase activity in homogenate of E. coli into which β-galactoside-α2,6-sialyltransferase gene from strain JT-ISH-224 is introduced

| Crude enzyme solution | Radioactivity |
|---|---|
| ISH224-N0C0 clone | + |
| ISH224-N1C0 clone | + |
| ISH224-N2C0 clone | + |
| ISH224-N3C0 clone | + |
| ISH224-N3.1C0 clone | − |
| Absence | − |

Reaction Conditions
Reaction composition:

| | |
|---|---|
| 3M NaCl | 5 μl |
| 45 mg/ml Lactose (in 20 mM cacodylate buffer (pH 5)) | 10 μl |
| Crude enzyme solution diluted 200-fold | 5 μl |
| 4.55 mM CMP-sialic acid (in 20 mM cacodylate buffer (pH 5)) + $^{14}$C-CMP-sialic acid | 5 μl |

Reaction time: 2 minutes
Reaction temperature: 30° C.

(5) Confirmation of β-galactoside-α2,6-sialyltransferase Activity

The crude enzyme solution prepared in (4) above from the ISH224-N1C0 or ISH224-N0C0 clone was used to examine whether sialyltransferase expressed by E. coli cells into which ISH224-N0C0/pTrc or ISH224-N1C0/pTrc had been introduced had β-galactoside-α2,6-sialyltransferase activity. As in the case of Example 1, pyridylaminated lactose (Galβ1-4Glc-PA, PA-Sugar Chain 026, Takara Bio Inc., Japan) was used as a glycosyl acceptor to carry out the enzymatic reaction. As a result, PA-6'-sialyllactose (Neu5Acα2-6Galβ1-4Glc-PA) was detected, as in the case of Example 1. Namely, sialyltransferases derived from both clone strains were found to have β-galactoside-α2,6-sialyltransferase activity. These results demonstrated that the β-galactoside-α2,6-sialyltransferase gene from Photobacterium sp. strain JT-ISH-224 was cloned and expressed in E. coli cells.

Example 3

Productivity of Recombinant β-Galactoside-α2,6-Sialyltransferase Derived from JT-ISH-224

Comparison Between ISH224-N0C0 and ISH224-N1C0 clones

A time-dependent induction experiment of protein expression was performed on the ISH224-N0C0 and ISH224-N1C0 clones obtained in Example 2. A single colony of E. coli TB1 having the expression vector pTrc99A carrying each clone was inoculated into LB medium (6 ml) containing an antibiotic, ampicillin (final concentration 100 μg/mL), and pre-cultured at 30° C. for about 8 hours. This pre-cultured solution was inoculated into LB medium (300 ml) containing and antibiotic, ampicillin (final concentration 100 μg/mL) and cultured with shaking at 30° C. When OD600 reached around 0.5, IPTG (isopropyl-β-D(−)-thiogalactopyranoside, Wako Pure Chemical Industries, Ltd., Japan) was added at a final concentration of 1 mM, followed by culturing with shaking at 30° C. At 4, 6, 22 and 28 hours after culturing, the cells in each culture solution were collected by centrifugation. These cells were suspended in 20 mM Bis-Tris buffer (pH 6.0) containing 0.336% 100 Triton® X-100, and ultrasonically homogenized under ice cooling. The resulting homogenate was defined as a crude enzyme solution, diluted 200-fold with 20 mM cacodylate buffer (pH 5.0) containing 0.336% Triton X®-100, and then provided for activity measurement. The reaction was carried out in duplicate. The reaction conditions are as indicated in the footnote of Table 2. As a result, as shown in Table 2 below, the ISH224-N0C0 clone showed maximum β-galactoside-α2,6-sialyltransferase activity at 4 hours after IPTG addition, and its productivity was 5,501 U/L of medium. On the other hand, the ISH224-N1C0 clone showed maximum β-galactoside-α2,6-sialyltransferase activity at 22 hours after IPTG addition, and its productivity was 10,776 U/L of medium.

TABLE 2

Sialyltransferase activity in homogenate of E. coli into which β-galactoside-α2,6-sialyltransferase gene from strain JT-ISH-224 is introduced

| Clone name | Hours after IPTG addition | Culture volume (L) | Buffer volume used for homogenization (ml) | Radio-activity (CPM) | Amount of transferred sialic acid (nmol) | Enzyme concentration in crude enzyme solution (unit/ml) | Total enzyme activity (unit) | Productivity (U/L of medium) |
|---|---|---|---|---|---|---|---|---|
| ISH224-N0C0 | 4 | 0.3 | 28.3 | 1235.5 | 1.46 | 58.3 | 1650 | 5501 |
| | 6 | 0.3 | 26.0 | 791.0 | 0.93 | 37.3 | 971 | 3236 |
| | 22 | 0.3 | 30.9 | 638.0 | 0.75 | 30.1 | 931 | 3102 |
| | 28 | 0.3 | 32.0 | 512.0 | 0.60 | 24.2 | 773 | 2578 |

TABLE 2-continued

Sialyltransferase activity in homogenate of *E. coli* into which β-galactoside-α2,6-sialyltransferase gene from strain JT-ISH-224 is introduced

| Clone name | Hours after IPTG addition | Culture volume (L) | Buffer volume used for homogenization (ml) | Radio-activity (CPM) | Amount of transferred sialic acid (nmol) | Enzyme concentration in crude enzyme solution (unit/ml) | Total enzyme activity (unit) | Productivity (U/L of medium) |
|---|---|---|---|---|---|---|---|---|
| ISH224-N1C0 | 4 | 0.3 | 26.0 | 142.5 | 0.17 | 6.8 | 177 | 589 |
|  | 6 | 0.3 | 26.0 | 311.0 | 0.37 | 14.8 | 385 | 1285 |
|  | 22 | 0.3 | 37.5 | 1809.0 | 2.16 | 86.2 | 3233 | 10776 |
|  | 28 | 0.3 | 38.6 | 1459.0 | 1.74 | 69.5 | 2684 | 8946 |

Reaction Conditions
Reaction composition:

| | |
|---|---|
| 3 M NaCl | 5 μl |
| 45 mg/ml Lactose (in 20 mM cacodylate buffer (pH 5)) | 10 μl |
| Crude enzyme solution diluted 200-fold | 5 μl |
| 4.55 mM CMP-sialic acid (in 20 mM cacodylate buffer (pH 5)) + $^{14}$C-CMP-sialic acid | 5 μl |

Reaction time: 1 minute
Reaction temperature: 30° C.

These results indicated that the productivity of β-galactoside-α2,6-sialyltransferase was higher in the ISH224-N1C0 clone than in the ISH224-N0C0 clone.

As has been shown before the filing of the present application, *Photobacterium damselae*-derived recombinant β-galactoside-α2,6-sialyltransferase, i.e., β-galactoside-α2,6-sialyltransferase produced by *E. coli* cells transformed with plasmid pEBSTΔ178 has a productivity of 224.5 U/L (Yamamoto, T., et al., J. Biochem., 120, 104-110 (1996)). When compared to this enzyme, JT-ISH-224-derived recombinant α2,6-sialyltransferase was found to have about 48-fold higher productivity. Likewise, as a microbial sialyltransferase, *Pasteurella multocida*-derived α2,3-sialyltransferase is known to have a high productivity of 6,000 U/L (Yu, H. et al., J. Am. Chem. Soc., 127, 17618-17619, 2005), although it is categorized as a different type of enzyme. When compared to this enzyme, JT-ISH-224-derived recombinant β-galactoside-α2,6-sialyltransferase was also found to have about 1.8-fold higher productivity.

Example 4-1

Extraction and Purification of β-galactoside-α2,6-sialyltransferase from ISH224-N1C0, and Amino-Terminal Amino Acid Sequencing of the Purified Protein (1) Extraction and Purification From colonies of ISH224-N1C0 subcultured on LBAmp agar plates, the cells were collected with a loop, inoculated into 6 ml-LB liquid medium (10 ml) supplemented with 30 μl of ×200 ampicillin (400 mg/20 ml), and cultured with shaking at 30° C. at 180 rpm for 8 hours.

Main culturing was accomplished in the following manner. 300 ml-LB medium supplemented with 1.5 ml of ×200 ampicillin (400 mg/20 ml) and 300 μl of 1M IPTG (1.192 g/5 ml) was charged into a 1000 ml baffle flask. The same medium was prepared in 9 flasks (2.7 L in total). Each flask was inoculated with the above culture solution (12 ml) and cultured with shaking at 30° C. at 180 rpm for 24 hours. The cultured medium was centrifuged to collect the cells (about 15 g on a wet weight basis).

The cells were suspended in 990 ml of 20 mM Bis-Tris buffer (pH 6.0) containing 0.336% Triton® X-100 to give a concentration of 1.6 g/26 ml, and ultrasonically homogenized under ice cooling. The cell homogenate was centrifuged at 4° C. at 100,000×g for 1 hour to obtain the supernatant.

This crude enzyme solution was loaded to an anion exchange column called HiLoad 26/10 Q SEPHAROSE® HP (Amersham), which had been equilibrated with 20 mM Bis-Tris buffer (pH 6.0) containing 0.336% Triton® X-100. The column was eluted with a linear gradient up to 1 M sodium chloride in 20 mM Bis-Tris buffer (pH 6.0) containing 0.336% Triton® X-100 to thereby collect an enzymatically active fraction eluted at around 0.25 M sodium chloride concentration.

The collected fraction was diluted with 20 mM phosphate buffer (pH 6.0) and loaded to hydroxyapatite (Bio-Rad) which had been equilibrated with 20 mM phosphate buffer (pH 6.0) containing 0.336% Triton® X-100, followed by elution with a linear gradient from 20 mM phosphate buffer (pH 6.0) containing 0.336% Triton® X-100 to 500 mM phosphate buffer (pH 6.0) containing 0.336% Triton® X-100 to thereby collect an enzymatically active fraction eluted at around 125 mM phosphate buffer concentration.

This fraction was loaded to a MONO Q® 5/50 GL (Amersham) anion exchange column. The column was eluted with a linear gradient up to 1 M sodium chloride in 20 mM Bis-Tris buffer (pH 6.0) containing 0.336% Triton X® 100 to thereby collect an enzymatically active fraction eluted at around 300 mM sodium chloride concentration.

The active fraction was electrophoresed on an SDS-polyacrylamide gel (the concentration of the acrylamide gel: 12.5%), indicating that the target enzyme showed a single band with a molecular weight of about 56,000. The specific activity of this purified fraction was about 9.4-fold higher than that of the cell homogenate (Table 3-1). These results indicated that JT-ISH-224-derived recombinant β-galactoside-α2,6-sialyltransferase N1C0 had a specific activity of 113 U/mg, which was about 21-fold higher than that (5.5 U/mg) of β-galactoside-α2,6-sialyltransferase derived from *Photobacterium damselae* strain JT0160 (J. Biochem., 120, 104-110, 1996, T. Yamamoto et al.). Likewise, *Pasteurella multocida*-derived β-galactoside-α2,3-sialyltransferase has a specific activity of 60 U/mg (Yu, H. et al., J. Am. Chem. Soc., 127, 17618-17619, 2005.), although it is categorized as a different type of enzyme. When compared to this enzyme, JT-ISH-224-derived recombinant β-galactoside-α2,6-sialyltransferase N1C0 is also found to have about 1.9-fold higher specific activity.

As to purification of β-galactoside-α2,6-sialyltransferase of the ISH224-N1C0 clone from a crude enzyme solution, Table 3-1 shows the enzyme activity of the sample after each of the purification steps mentioned above. The enzyme activity was measured by the method reported in J. Biochem. 120, 104-110 (1996), in the same manner as described in Example 1 under conditions as indicated in the footnote of Table 3-1. For protein quantification, a Coomassie Protein Assay Reagent (PIERCE) was used according to the instruction manual attached thereto. One enzyme unit (1U) was defined as the amount of enzyme required to transfer 1 micromole of sialic acid per minute.

[Table 3-1]
Table 3-1: Purification of β-galactoside-α2,6-sialyltransferase Derived from Strain ISH224-N1C0 from Crude Enzyme Solution

TABLE 3-1

Purification of β-galactoside-α2,6-sialyltransferase derived from strain ISH224-N1C0 from crude enzyme solution

| Purification step | Volume (ml) | Total protein (mg) | Total activity (U) | Specific activity (U/mg) | Yield (%) | Purification degree (fold) |
|---|---|---|---|---|---|---|
| Crude enzyme solution | 237.5 | 1,100 | 13167 | 12.0 | 100 | 1.0 |
| Q SEPHAROSE ™ | 64.0 | 371 | 11794 | 31.8 | 90 | 2.7 |
| Hydroxyapatite | 180.0 | 138 | 9448 | 68.3 | 72 | 5.7 |
| MONO Q ® | 4.5 | 24.1 | 2720 | 113 | 21 | 9.4 |

| | |
|---|---|
| 3 M NaCl | 5 μl |
| 360 mM Lactose | 10 μl |
| 1 M Bis-Tris buffer (pH 6) | 3 μl |
| Water | 2 μl |
| Enzyme solution | 5 μl |
| 14 mM CMP-sialic acid (in 20 mM Bis-Tris buffer (pH 6)) + $^{14}$C-CMP-sialic acid | 5 μl |

Reaction time: 5 minutes
Reaction temperature: 25° C.

(2) Amino-Terminal Amino Acid Sequencing

The enzyme solution purified to a single band in (1) above was electrophoresed on an SDS-polyacrylamide gel (the concentration of the acrylamide gel: 12.5%). After electrophoresis, the protein was transferred onto a PVDF membrane and stained with CBB. A band region of interest was then excised and analyzed for its amino acid sequence with a Procise 494 HT Protein Sequencing System (Applied Biosystems). As a result, a sequence whose amino-terminus started with serine was determined up to the 15th residue (Ser Glu Glu Asn Thr Gln Ser Ile Ile Lys Asn Asp Ile Asn Lys) (SEQ ID NO: 18). This result suggests that in the β-galactoside-α2,6-sialyltransferase protein produced by E. coli cells transformed with the ISH224-N1C0 clone, its amino-terminal methionine was processed within the E. coli cells.

Example 4-2

Extraction and Purification of β-galactoside-α2,6-sialyltransferase from ISH224-N3C0

(1) Extraction and Purification

From colonies of ISH224-N3C0 subcultured on LBAmp agar plates, the cells were collected with a loop, inoculated into 6 ml-LB liquid medium (10 ml) supplemented with 30 μl of ×200 ampicillin (400 mg/20 ml), and cultured with shaking at 30° C. at 180 rpm for 8 hours.

Main culturing was accomplished in the following manner. 300 ml-LB medium supplemented with 1.5 ml of ×200 ampicillin (400 mg/20 ml) and 300 μl of 1M IPTG (1.192 g/5 ml) was charged into a 1000 ml baffle flask. The same medium was prepared in 18 flasks (5.4 L in total). Each flask was inoculated with the above culture solution (12 ml) and cultured with shaking at 30° C. at 180 rpm for 24 hours. The cultured medium was centrifuged to collect the cells (about 33.1 g on a wet weight basis).

The cells were suspended in 538.5 ml of 20 mM Bis-Tris buffer (pH 6.0) containing 0.336% Triton® X-100 to give a concentration of 1.6 g/26 ml, and ultrasonically homogenized under ice cooling. The cell homogenate was centrifuged at 4° C. at 100,000×g for 1 hour to obtain the supernatant.

This crude enzyme solution was loaded to an anion exchange column called HiLoad 26/10 Q SEPHAROSE® HP (Amersham), which had been equilibrated with 20 mM Bis-Tris buffer (pH 6.0) containing 0.336% Triton® X-100. The column was eluted with a linear gradient up to 1 M sodium chloride in 20 mM Bis-Tris buffer (pH 6.0) containing 0.336% Triton® X-100 to thereby collect an enzymatically active fraction eluted at around 0.25 M sodium chloride concentration.

The collected fraction was diluted with 20 mM phosphate buffer (pH 6.0) and loaded to hydroxyapatite (Bio-Rad) which had been equilibrated with 20 mM phosphate buffer (pH 6.0) containing 0.336% Triton® X-100, followed by elution with a linear gradient from 20 mM phosphate buffer (pH 6.0) containing 0.336% Triton® X-100 to 500 mM phosphate buffer (pH 6.0) containing 0.336% Triton® X-100 to thereby collect an enzymatically active fraction eluted at around 125 mM phosphate buffer concentration. This fraction was loaded to a MONO Q® 5/50 GL (Amersham) anion exchange column. The column was eluted with a linear gradient up to 1 M sodium chloride in 20 mM Bis-Tris buffer (pH 6.0) containing 0.336% Triton® X-100 to thereby collect an enzymatically active fraction eluted at around 300 mM sodium chloride concentration.

The active fraction was electrophoresed on an SDS-polyacrylamide gel (the concentration of the acrylamide gel: 12.5%), indicating that the target enzyme showed a single band with a molecular weight of about 40,000. The specific activity of this purified fraction was about 131.5-fold higher than that of the cell homogenate (Table 3-2). These results indicated that JT-ISH-224-derived recombinant β-galactoside-α2,6-sialyltransferase N3C0 had a specific activity of 264 U/mg, which was about 48-fold higher than that (5.5 U/mg) of β-galactoside-α2,6-sialyltransferase derived from Photobacterium damselae strain JT0160 (J. Biochem., 120, 104-110, 1996, T. Yamamoto et al.). Likewise, Pasteurella multocida-derived β-galactoside-α2,3-sialyltransferase has a specific activity of 60 U/mg (Yu, H. et al., J. Am. Chem. Soc., 127, 17618-17619, 2005.), although it is categorized as a different type of enzyme. When compared to this enzyme, JT-ISH-224-derived recombinant β-galactoside-α2,6-sialyltransferase N3C0 is also found to have about 4.4-fold higher specific activity.

As to purification of β-galactoside-α2,6-sialyltransferase N3C0 of the ISH224-N3C0 clone from a crude enzyme solution, Table 3-2 shows the enzyme activity of the sample after each of the purification steps mentioned above. The enzyme activity was measured by the method reported in J. Biochem. 120, 104-110 (1996), in the same manner as described in Example 1 under conditions as indicated in the footnote of Table 3-2. For protein quantification, a Coomassie Protein Assay Reagent (PIERCE) was used according to the instruction manual attached thereto. One enzyme unit (1U) was defined as the amount of enzyme required to transfer 1 micromole of sialic acid per minute.

[Table 3-2]

TABLE 3-2

Purification of β-galactoside-α2,6-sialyltransferase derived from strain ISH224-N3C0 from crude enzyme solution

| Purification step | Volume (ml) | Total protein (mg) | Total activity (U) | Specific activity (U/mg) | Yield (%) | Purification degree (fold) |
|---|---|---|---|---|---|---|
| Crude enzyme solution | 505.0 | 2445 | 4911 | 2.0 | 100 | 1.0 |
| Q SEPHAROSE ™ | 39.0 | 136 | 3614 | 26.5 | 74 | 13.2 |
| Hydroxyapatite | 6.0 | 6.6 | 997 | 151 | 20 | 75.4 |
| MONO Q ® | 1.5 | 3.1 | 808 | 264 | 16 | 131.5 |

Reaction Conditions
Reaction composition:

| | |
|---|---|
| 3 M NaCl | 5 µl |
| 360 mM Lactose | 10 µl |
| 1 M Cacodylate buffer (pH 5) | 3 µl |
| Water | 2 µl |
| Enzyme solution | 5 µl |
| 14 mM CMP-sialic acid (in 20 mM cacodylate buffer (pH 5)) + $^{14}$C-CMP-sialic acid | 5 µl |

Reaction time: 5 minutes
Reaction temperature: 30° C.

Example 5

Optimum pH, Optimum Temperature and Optimum Salt Concentration for Enzyme Activity of Recombinant β-galactoside-α2,6-sialyltransferase N1C0 Derived from JT-ISH-224

The purified enzyme prepared in Example 4-1 was used to examine the optimum pH, optimum temperature and optimum salt concentration for JT-ISH-224-derived recombinant β-galactoside-α2,6-sialyltransferase N1C0.
(1) Optimum pH for Enzyme Activity of JT-ISH-224-Derived Recombinant β-galactoside-α2,6-sialyltransferase N1C0

Acetate buffer (pH 4.0, pH 4.5 and pH 5.0), cacodylate buffer (pH 5.0, pH 5.5, pH 6.0, pH 6.5 and pH 7.0), phosphate buffer (pH 7.0, pH 7.5 and pH 8.0) and TAPS buffer (pH 8.0, pH 8.5 and pH 9.0) were prepared and used for enzyme activity measurement at 25° C. at various pH values.

As a result, as shown in FIG. 2-1, the enzyme activity was maximum at pH 5.0. It should be noted that enzyme activity at each pH was expressed as relative activity, assuming that the enzyme activity at pH 5.0 was set to 100.
(2) Optimum Temperature for Enzyme Activity of JT-ISH-224-Derived Recombinant β-galactoside-α2,6-sialyltransferase N1C0

The enzyme activity was measured at an interval of 5° C. starting from 10° C. up to 50° C. using cacodylate buffer (pH 5.0).

As a result, as shown in FIG. 2-2, the enzyme activity was maximum at 30° C. It should be noted that enzyme activity at each temperature was expressed as relative activity, assuming that the enzyme activity at 30° C. was set to 100.
(3) Optimum Salt Concentration for Enzyme Activity of JT-ISH-224-Derived Recombinant β-galactoside-α2,6-sialyltransferase N1C0

The enzyme activity was measured at 30° C. using cacodylate buffer (pH 5.0) by adjusting the NaCl concentration in the reaction solution to 0 M, 0.1 M, 0.25 M, 0.5 M, 0.75 M, 1.0 M, 1.5 M or 2.0 M.

As a result, as shown in FIG. 2-3, the enzyme activity was maximum between 0.5 M and 0.75 M. Moreover, the enzyme activity was maintained at substantially the same level between 0 M and 1.0 M. It should be noted that enzyme activity at each NaCl concentration was expressed as relative activity, assuming that the enzyme activity at 0 M NaCl concentration was set to 100.

Example 6

Comparison of Acceptor Substrate (Monosaccharide, Disaccharide and Trisaccharide) Specificity Between JT-ISH-224-Derived Recombinant β-galactoside-α2, 6-sialyltransferase and Strain JT0160-Derived β-galactoside-α2,6-sialyltransferase (Known Enzyme)

(Material and Method)

Cell homogenates prepared from E. coli cells into which JT-ISH-224-derived N1C0 had been introduced and from Photobacterium damselae strain JT0160 were each purified by ion exchange chromatography and hydroxyapatite chromatography to give an electrophoretically single band. The thus purified β-galactoside-α2,6-sialyltransferases were used in the following experiment in order to examine the presence or absence of sialyltransferase activity toward various monosaccharides, disaccharides and trisaccharides.

Sialic Acid Transfer Reaction Using Various Glycosyl Acceptor Substrates

A reaction solution (24 µl) was prepared to contain CMP-$^{14}$C-NeuAc-containing CMP-NeuAc as a glycosyl donor substrate (10.9 nmol (8485 cpm), final concentration in the reaction solution: 0.455 mM), any of various glycosyl acceptor substrates dissolved in 20 mM cacodylate buffer (pH 5.0) (1 µmol, final concentration in the reaction solution: 42 mM), sialyltransferase (3.0 mU for JT-ISH-224-derived N1C0, 4.3 mU for JT0160) and NaCl (final concentration in the reaction solution: 500 mM), and reacted at 30° C. for 2 minutes or 60 minutes. The monosaccharides used as glycosyl acceptor substrates were the following 8 types: methyl-α-D-galactopyranoside (Gal-α-OMe), methyl-β-D-galactopyranoside (Gal-β-OMe), methyl-α-D-glucopyranoside (Glc-α-OMe), methyl-β-D-glucopyranoside (Glc-β-OMe), methyl-α-D-mannopyranoside (Man-α-OMe), methyl-β-D-mannopyranoside (Man-β-OMe), N-acetylgalactosamine (GalNAc), and N-acetylglucosamine (GalNAc). The disaccharides used were the following 5 types: lactose (Gal-β1,4-Glc), N-acetyllactosamine (Gal-β1,4-GlcNAc), methyl-β-D-galactopyranosyl-β1,3-N-acetylglucosaminide (Gal-β1,3-GlcNAc-β-OMe), methyl-α-D-galactopyranosyl-α1,3-galactopyranoside (Gal-α1,3-Gal-α-OMe), and methyl-β-D-galactopyranosyl-β1,3-galactopyranoside (Gal-β1,3-Gal-β-OMe). The trisaccharide used was 2'-fucosyllactose (Fuc-α1,2-Galβ1,4-Glc). It should be noted that the final concentration was set to 8.4 mM for the sugar chains shown in Table 4-2, i.e., methyl-α-D-galactopyranosyl-α1,3-galactosaminide (Gal-α1,3-Gal-α-OMe), methyl-β-D-galactopyranosyl-β1,3-galactosaminide (Gal-β1,3-Gal-β-OMe) and 2'-fucosyllactose (Fuc-α1,2-Galβ1,4-Glc).

After completion of the enzymatic reaction, 1.98 ml of 5 mM phosphate buffer (pH 6.8) was added to the reaction solution to stop the enzymatic reaction. Then, the enzymatic reaction solution was diluted with 5 mM phosphate buffer (Ph 6.8) and applied in a volume of 2 ml to a AG1-x2Resin ($PO_4^{3-}$ form, 0.2×2 cm) column. This column was prepared as follows: AG1-x2Resin (OH⁻ form, BIO-RAD) was suspended in 1 M phosphate buffer (pH 6.8), and after 30 minutes, the resin was washed with distilled water and then suspended in distilled water. The eluate (0 to 2 ml) from this column was measured for its radioactivity. The eluate from this column contains the unreacted glycosyl acceptor substrate and the $^{14}$C-NeuAc (N-acetylneuraminic acid)-bound reaction product which was generated by the reaction, whereas unreacted CMP-$^{14}$C-NeuAc is still retained on the column. Thus, the radioactivity of $^{14}$C from each sialic acid-containing sugar chain generated as a result of the enzymatic reaction arises exclusively from the reaction product, so that the radioactivity of this fraction can be used to calculate the enzyme activity.

In the manner described above, the radioactivity of NeuAc transferred to each glycosyl acceptor substrate was measured to calculate the amount of transferred sialic acid.

(Results)

Sialic acid was found to be transferred to all the 14 monosaccharides, disaccharides and trisaccharide used as glycosyl acceptor substrates in this experiment (Tables 4-1 and 4-2). JT-ISH-224-derived recombinant β-galactoside-α2,6-sialyltransferase showed high glycosyltransferase activity over a wide range of acceptor substrates, when compared to the known β-galactoside-α2,6-sialyltransferase derived from the strain JT0160. More specifically, JT-ISH-224-derived recombinant β-galactoside-α2,6-sialyltransferase N1C0 showed higher activity than the known β-galactoside-α2,6-sialyltransferase derived from the strain JT0160 in the following 6 glycosyl acceptors: methyl-β-D-galactopyranoside, N-acetylgalactosamine, N-acetyllactosamine, methyl-β-D-galactopyranosyl-β1,3-N-acetylglucosaminide, methyl-β-D-galactopyranosyl-β1,3-galactopyranoside and 2'-fucosyllactose. Thus, this recombinant enzyme was found to have a wider range of acceptor substrate specificity. It should be noted that the relative activity toward each acceptor substrate was calculated assuming that the sialyltransferase activity toward lactose was set to 100.

TABLE 4-1

Acceptor substrate specificity of β-galactoside-α2,6-sialyltransferase derived from strain ISH224-N1C0 (No. 1)

| Acceptor substrate | | JT-ISH-224-N1C0 Sialyltransferase activity | | JT0160 Sialyltransferase activity | |
|---|---|---|---|---|---|
| Name | Structural formula | nmol/min | Relative activity (%) | nmol/min | Relative activity (%) |
| Methylαgalactopyranoside | Galα-OMe | 0.038 | 2.0 | 0.017 | 0.8 |
| Methylβgalactopyranoside | Galβ-OMe | 1.110 | 59.2 | 0.355 | 15.6 |
| Methylαglucopyranoside | Glcα-OMe | 0.008 | 0.4 | 0.007 | 0.3 |
| Methylβglucopyranoside | Glcβ-OMe | 0.009 | 0.5 | 0.005 | 0.2 |
| Methylαmannopyranoside | Manα-OMe | 0.010 | 0.5 | 0.005 | 0.2 |
| Methylβmannopyranoside | Manβ-OMe | 0.008 | 0.4 | 0.007 | 0.3 |
| N-Acetylgalactosamine | GalNAc | 0.228 | 12.2 | 0.050 | 2.2 |
| N-Acetylglucosamine | GlcNAc | 0.008 | 0.4 | 0.007 | 0.3 |
| Lactose | Galβ1,4-Glc | 1.875 | 100.0 | 2.277 | 100.0 |
| N-Acetyllactosamine | Gatβ1,4-GlcNAc | 1.861 | 99.3 | 0.345 | 15.1 |
| Methylβ-galactopyranosylβ1,3-N-acetylglucosaminide | Galβ1,3-GlcNAcβ-OMe | 1.435 | 76.5 | 0.878 | 38.6 |

TABLE 4-2

Acceptor substrate specificity of β-galactoside-α2,6-sialyltransferase derived from strain ISH224-N1C0 (No. 2)

| Acceptor substrate | | JT-ISH-224-N1C0 Sialyltransferase activity | | JT0160 Sialyltransferase activity | |
|---|---|---|---|---|---|
| Name | Structural formula | nmol/min | Relative activity (%) | nmol/min | Relative activity (%) |
| Methylαgalactopyranosyl α1,3-galactopyranoside | Galα1,3-Galα-OMe | 0.023 | 1.6 | 0.007 | 0.5 |
| Methylβgalactopyranosyl β1,3-galactopyranoside | Galβ1,3-Galβ-OMe | 0.964 | 67.5 | 0.176 | 13.9 |

TABLE 4-2-continued

Acceptor substrate specificity of β-galactoside-α2,6-sialyltransferase
derived from strain ISH224-N1C0 (No. 2)

| Acceptor substrate | | JT-ISH-224-N1C0 Sialyltransferase activity | | JT0160 Sialyltransferase activity | |
|---|---|---|---|---|---|
| Name | Structural formula | nmol/min | Relative activity (%) | nmol/min | Relative activity (%) |
| 2'-Fucosyllactose | Fuc-α1,2-Galβ1,4-Glc | 1.316 | 92.1 | 0.636 | 50.3 |
| Lactose | Galβ1,4-Glc | 1.428 | 100.0 | 1.264 | 100.0 |

Example 7

Comparison of Acceptor Substrate Specificity Toward Glycoprotein Between JT-ISH-224-Derived Recombinant β-galactoside-α2,6-sialyltransferase and Strain JT0160-Derived β-galactoside-α2,6-sialyltransferase (Known Enzyme)

As a glycosyl acceptor substrate, asialofetuin was used. Asialofetuin (2 mg) was dissolved in 1 ml of 20 mM Bis-Tris buffer (pH 6.0) and used as a glycosyl acceptor substrate solution. As a glycosyl donor substrate, CMP-NeuAc was used. The glycosyl acceptor substrate solution (40 µl), the glycosyl donor substrate (5 µl) and either of the enzyme solutions (5 µl, 10 mU each) were mixed and incubated at 25° C. for 2 hours to cause sialic acid transfer reaction. After completion of the reaction, the reaction solution was gel-filtered by being applied to a SEPHADEX® G-50 Superfine (0.8×18.0 cm) equilibrated with 0.1 M sodium chloride. A glycoprotein-containing eluate fraction (2-4 ml fraction) from gel filtration was collected and measured for its radioactivity using a liquid scintillation counter to quantify sialic acid transferred to the glycosyl acceptor substrate.

As a result, both enzymes were found to have the ability to transfer sialic acid to asialofetuin. Moreover, JT-ISH-224-derived β-galactoside-α2,6-sialyltransferase (N1C0) was found to achieve higher efficiency of sialic acid transfer than β-galactoside-α2,6-sialyltransferase derived from *Photobacterium damselae* strain JT0160.

TABLE 5

Acceptor substrate specificity of β-galactoside-α2,6-sialyltransferase
derived from strain ISH224-N1C0 (No. 3)

| Enzyme solution | Radioactivity (cpm) |
|---|---|
| JT-ISH-224-N1C0 | 3051 |
| JT0160 | 2150 |
| Absence | 9 |

Reaction Conditions
Reaction composition:

| | |
|---|---|
| Asialofetuin solution | 10 µl |
| Enzyme solution | 5 µl |
| 5 mM CMP-sialic acid (in 20 mM cacodylate buffer (pH 5)) + $^{14}$C-CMP-sialic acid | 5 µl |

INDUSTRIAL APPLICABILITY

By providing a novel β-galactoside-α2,6-sialyltransferase and a nucleic acid encoding the same, the present invention provides a means for synthesizing and producing sugar chains which are being shown to have important functions in the body. In particular, sialic acid is often located at the nonreducing termini of complex carbohydrate sugar chains in the body and is a very important sugar in terms of sugar chain functions. Thus, sialyltransferase is one of the most in demand enzymes among glycosyltransferases. The novel sialyltransferase of the present invention can be used for the development of pharmaceuticals, functional foods and other products where sugar chains are applied.

The invention claimed is:

1. An isolated nucleic acid encoding a protein having β-galactoside-α2,6-sialyltransferase activity, wherein the protein comprises an amino acid sequence selected from the group consisting of SEQ ID NO: 2, amino acid residues 15-514 of SEQ ID NO: 2, SEQ ID NO: 4 and SEQ ID NO: 12.

2. An isolated nucleic acid encoding a protein having β-galactoside-α2,6-sialyltransferase activity, wherein the protein comprises:
   (a) an amino acid sequence comprising at least 90% sequence identity with an amino acid sequence selected from the group consisting of SEQ ID NO: 2, amino acid residues 15-514 of SEQ ID NO: 2, SEQ ID NO: 4 and SEQ ID NO: 12; or
   (b) an amino acid sequence comprising at least 95% sequence identity with an amino acid sequence selected from the group consisting of SEQ ID NO: 2, amino acid residues 15-514 of SEQ ID NO: 2, SEQ ID NO: 4 and SEQ ID NO: 12.

3. An isolated nucleic acid encoding a protein having β-galactoside-α2,6-sialyltransferase activity, wherein the nucleic acid comprises a nucleotide sequence selected from the group consisting of SEQ ID NO: 1, nucleotides 43-1545 of SEQ ID NO: 1, SEQ ID NO: 3 and SEQ ID NO: 11.

4. An isolated nucleic acid encoding a protein having β-galactoside-α2,6-sialyltransferase activity, wherein the nucleic acid comprises:
   (a) a nucleotide sequence comprising at least 90% sequence identity with a nucleotide sequence selected from the group consisting of SEQ ID NO: 1, nucleotides 43-1545 of SEQ ID NO: 1, SEQ ID NO: 3 and SEQ ID NO: 11, or
   (b) a nucleotide sequence hybridizable under hybridization conditions of 65° C., 6×SSC, and washing conditions of 65° C., 0.2×SSC, 0.1% SDS with the full complement of a nucleotide sequence selected from the group consisting of SEQ ID NO: 1, nucleotides 43-1545 of SEQ ID NO: 1, SEQ ID NO: 3 and SEQ ID NO: 11.

5. An expression vector comprising the nucleic acid of claim 2.

6. A host cell transformed with the expression vector of claim 5.

7. An isolated microorganism belonging to the genus *Photobacterium*, which expresses a protein encoded by the nucleic acid of claim 2.

8. A method for producing a protein having β-galactoside-α2,6-sialyltransferase activity, which comprises the following steps:
   1) culturing a microorganism producing a β-galactoside-α2,6-sialyltransferase encoded by the nucleic acid of claims 2; and
   2) isolating the β-galactoside-α2,6-sialyltransferase from the cultured microorganism or the culture supernatant.

9. The method of claim 8, wherein the microorganism is *Photobacterium* sp, strain JT-ISH-224 (Accession No. NITE BP-87).

10. A method for producing a recombinant protein having β-galactoside-α2,6-sialyltransferase activity, which comprises the following steps:
   1) transforming a host cell with an expression vector comprising the nucleic acid of claim 2;
   2) culturing the resulting transformant; and
   3) isolating the protein having β-galactoside-α2,6-sialyltransferase activity from the cultured transformant or its culture supernatant.

* * * * *

UNITED STATES PATENT AND TRADEMARK OFFICE
CERTIFICATE OF CORRECTION

| | |
|---|---|
| PATENT NO. | : 8,187,838 B2 |
| APPLICATION NO. | : 12/789167 |
| DATED | : May 29, 2012 |
| INVENTOR(S) | : Hiroshi Tsukamoto et al. |

It is certified that error appears in the above-identified patent and that said Letters Patent is hereby corrected as shown below:

ON THE TITLE PAGE:

Please insert the following:

-- (30)   Foreign Application Priority Data

Mar. 14, 2006   (WO)   ...........................   PCT/JP2006/304993 --.

Signed and Sealed this
Ninth Day of October, 2012

David J. Kappos
*Director of the United States Patent and Trademark Office*

SEQUENCE LISTING

```
<160> NUMBER OF SEQ ID NOS: 18

<210> SEQ ID NO 1
<211> LENGTH: 1545
<212> TYPE: DNA
<213> ORGANISM: Photobacterium sp.
<220> FEATURE:
<221> NAME/KEY: CDS
<222> LOCATION: (1)..(1545)
<223> OTHER INFORMATION: alpha-2,6-sialyltransferase

<400> SEQUENCE: 1 atg aaa aac ttt tta tta tta act tta ata tta ctt act gct tgt aat    48
Met Lys Asn Phe Leu Leu Leu Thr Leu Ile Leu Leu Thr Ala Cys Asn
1               5                   10                  15
```

| | | |
|---|---|---|
| aat tca gaa gaa aat aca caa tct att att aaa aat gat att aat aaa<br>Asn Ser Glu Glu Asn Thr Gln Ser Ile Ile Lys Asn Asp Ile Asn Lys<br>20 25 30 | 96 | |
| act att att gat gag gag tat gtt aat tta gag cca att aat caa tca<br>Thr Ile Ile Asp Glu Glu Tyr Val Asn Leu Glu Pro Ile Asn Gln Ser<br>35 40 45 | 144 | |
| aac atc tct ttt aca aaa cac tct tgg gta caa act tgt ggt acg caa<br>Asn Ile Ser Phe Thr Lys His Ser Trp Val Gln Thr Cys Gly Thr Gln<br>50 55 60 | 192 | |
| caa cta tta aca gaa caa aat aaa gag tca ata tca tta tct gta gtg<br>Gln Leu Leu Thr Glu Gln Asn Lys Glu Ser Ile Ser Leu Ser Val Val<br>65 70 75 80 | 240 | |
| gcg cca cga tta gat gac gat gaa aag tac tgc ttt gat ttt aat ggt<br>Ala Pro Arg Leu Asp Asp Asp Glu Lys Tyr Cys Phe Asp Phe Asn Gly<br>85 90 95 | 288 | |
| gtt agt aat aaa ggt gaa aaa tat ata aca aaa gta aca tta aac gta<br>Val Ser Asn Lys Gly Glu Lys Tyr Ile Thr Lys Val Thr Leu Asn Val<br>100 105 110 | 336 | |
| gtg gct cca tct tta gag gtt tat gtt gat cat gca tct ctt cca act<br>Val Ala Pro Ser Leu Glu Val Tyr Val Asp His Ala Ser Leu Pro Thr<br>115 120 125 | 384 | |
| ctt cag cag cta atg gat att att aaa tcg gaa gaa gaa aat cct aca<br>Leu Gln Gln Leu Met Asp Ile Ile Lys Ser Glu Glu Glu Asn Pro Thr<br>130 135 140 | 432 | |
| gca caa aga tat ata gct tgg ggg aga ata gtt ccg act gat gag caa<br>Ala Gln Arg Tyr Ile Ala Trp Gly Arg Ile Val Pro Thr Asp Glu Gln<br>145 150 155 160 | 480 | |
| atg aaa gag tta aat att aca tcg ttt gca ttg ata aat aac cat aca<br>Met Lys Glu Leu Asn Ile Thr Ser Phe Ala Leu Ile Asn Asn His Thr<br>165 170 175 | 528 | |
| cca gct gac tta gta caa gaa att gtt aag caa gca caa aca aag cat<br>Pro Ala Asp Leu Val Gln Glu Ile Val Lys Gln Ala Gln Thr Lys His<br>180 185 190 | 576 | |
| aga ttg aat gtt aaa ctt agc tct aac act gct cat tca ttt gat aat<br>Arg Leu Asn Val Lys Leu Ser Ser Asn Thr Ala His Ser Phe Asp Asn<br>195 200 205 | 624 | |
| tta gtg cca ata cta aaa gaa tta aat tcg ttt aat aac gtt acg gta<br>Leu Val Pro Ile Leu Lys Glu Leu Asn Ser Phe Asn Asn Val Thr Val<br>210 215 220 | 672 | |
| aca aat ata gat tta tat gat gat ggt tca gca gaa tat gta aat tta<br>Thr Asn Ile Asp Leu Tyr Asp Asp Gly Ser Ala Glu Tyr Val Asn Leu<br>225 230 235 240 | 720 | |
| tat aac tgg aga gat aca tta aat aaa aca gat aat tta aaa att ggt<br>Tyr Asn Trp Arg Asp Thr Leu Asn Lys Thr Asp Asn Leu Lys Ile Gly<br>245 250 255 | 768 | |
| aaa gat tat ctt gag gat gtc att aat ggt atc aat gaa gac act tca<br>Lys Asp Tyr Leu Glu Asp Val Ile Asn Gly Ile Asn Glu Asp Thr Ser<br>260 265 270 | 816 | |
| aat aca gga aca tca tct gtt tat aac tgg caa aaa cta tat cca gct<br>Asn Thr Gly Thr Ser Ser Val Tyr Asn Trp Gln Lys Leu Tyr Pro Ala<br>275 280 285 | 864 | |
| aac tac cat ttt tta aga aaa gat tat tta act tta gaa cca tca tta<br>Asn Tyr His Phe Leu Arg Lys Asp Tyr Leu Thr Leu Glu Pro Ser Leu<br>290 295 300 | 912 | |
| cat gag tta cga gac tat att ggt gat agt tta aag caa atg caa tgg<br>His Glu Leu Arg Asp Tyr Ile Gly Asp Ser Leu Lys Gln Met Gln Trp<br>305 310 315 320 | 960 | |
| gat ggt ttc aaa aaa ttc aat agc aaa caa caa gaa tta ttc tta tcg<br>Asp Gly Phe Lys Lys Phe Asn Ser Lys Gln Gln Glu Leu Phe Leu Ser<br>325 330 335 | 1008 | |

| | | | | | | | | | | | | | | | |
|---|---|---|---|---|---|---|---|---|---|---|---|---|---|---|---|
| att | gtt | aat | ttt | gac | aaa | caa | aaa | tta | caa | aat | gaa | tat | aat | tca | tct | 1056 |
| Ile | Val | Asn | Phe | Asp | Lys | Gln | Lys | Leu | Gln | Asn | Glu | Tyr | Asn | Ser | Ser |
| | | 340 | | | | | 345 | | | | | 350 | | | |
| aat | tta | cca | aac | ttt | gtg | ttt | aca | ggt | acg | act | gta | tgg | gct | ggt | aac | 1104 |
| Asn | Leu | Pro | Asn | Phe | Val | Phe | Thr | Gly | Thr | Thr | Val | Trp | Ala | Gly | Asn |
| | | | 355 | | | | | 360 | | | | | 365 | | |
| cat | gaa | aga | gag | tat | tat | gcg | aaa | caa | caa | att | aat | gtc | att | aat | aat | 1152 |
| His | Glu | Arg | Glu | Tyr | Tyr | Ala | Lys | Gln | Gln | Ile | Asn | Val | Ile | Asn | Asn |
| | 370 | | | | | 375 | | | | | 380 | | | | |
| gca | att | aat | gaa | tcg | agc | cca | cat | tat | tta | ggc | aat | agt | tat | gat | ttg | 1200 |
| Ala | Ile | Asn | Glu | Ser | Ser | Pro | His | Tyr | Leu | Gly | Asn | Ser | Tyr | Asp | Leu |
| 385 | | | | | 390 | | | | | 395 | | | | | 400 |
| ttc | ttc | aaa | ggt | cac | cct | ggt | ggc | ggt | atc | att | aat | aca | tta | ata | atg | 1248 |
| Phe | Phe | Lys | Gly | His | Pro | Gly | Gly | Gly | Ile | Ile | Asn | Thr | Leu | Ile | Met |
| | | | | 405 | | | | | 410 | | | | | 415 | |
| caa | aac | tat | cct | tca | atg | gtt | gat | att | cca | tca | aaa | ata | tca | ttt | gaa | 1296 |
| Gln | Asn | Tyr | Pro | Ser | Met | Val | Asp | Ile | Pro | Ser | Lys | Ile | Ser | Phe | Glu |
| | | | 420 | | | | | 425 | | | | | 430 | | |
| gtt | ttg | atg | atg | aca | gat | atg | ctt | cct | gat | gca | gtt | gct | ggt | ata | gcg | 1344 |
| Val | Leu | Met | Met | Thr | Asp | Met | Leu | Pro | Asp | Ala | Val | Ala | Gly | Ile | Ala |
| | | 435 | | | | | 440 | | | | | 445 | | | |
| agc | tct | tta | tat | ttc | acg | ata | cca | gct | gaa | aaa | att | aaa | ttt | ata | gtt | 1392 |
| Ser | Ser | Leu | Tyr | Phe | Thr | Ile | Pro | Ala | Glu | Lys | Ile | Lys | Phe | Ile | Val |
| | 450 | | | | | 455 | | | | | 460 | | | | |
| ttt | aca | tcg | aca | gaa | act | ata | act | gat | cgt | gaa | act | gct | ttg | aga | agt | 1440 |
| Phe | Thr | Ser | Thr | Glu | Thr | Ile | Thr | Asp | Arg | Glu | Thr | Ala | Leu | Arg | Ser |
| 465 | | | | | 470 | | | | | 475 | | | | | 480 |
| cct | tta | gtt | caa | gta | atg | ata | aaa | cta | ggt | att | gta | aaa | gaa | gag | aat | 1488 |
| Pro | Leu | Val | Gln | Val | Met | Ile | Lys | Leu | Gly | Ile | Val | Lys | Glu | Glu | Asn |
| | | | | 485 | | | | | 490 | | | | | 495 | |
| gta | ctt | ttt | tgg | gct | gat | ctg | cca | aat | tgt | gaa | aca | ggt | gtt | tgt | att | 1536 |
| Val | Leu | Phe | Trp | Ala | Asp | Leu | Pro | Asn | Cys | Glu | Thr | Gly | Val | Cys | Ile |
| | | | | 500 | | | | | 505 | | | | | 510 | |
| gca | gtc | tag | | | | | | | | | | | | | | 1545 |
| Ala | Val | | | | | | | | | | | | | | |

<210> SEQ ID NO 2
<211> LENGTH: 514
<212> TYPE: PRT
<213> ORGANISM: Photobacterium sp.

<400> SEQUENCE: 2

Met Lys Asn Phe Leu Leu Leu Thr Leu Ile Leu Leu Thr Ala Cys Asn
1               5                   10                  15

Asn Ser Glu Glu Asn Thr Gln Ser Ile Ile Lys Asn Asp Ile Asn Lys
            20                  25                  30

Thr Ile Ile Asp Glu Glu Tyr Val Asn Leu Glu Pro Ile Asn Gln Ser
        35                  40                  45

Asn Ile Ser Phe Thr Lys His Ser Trp Val Gln Thr Cys Gly Thr Gln
    50                  55                  60

Gln Leu Leu Thr Glu Gln Asn Lys Glu Ser Ile Ser Leu Ser Val Val
65                  70                  75                  80

Ala Pro Arg Leu Asp Asp Glu Lys Tyr Cys Phe Asp Phe Asn Gly
                85                  90                  95

Val Ser Asn Lys Gly Glu Lys Tyr Ile Thr Lys Val Thr Leu Asn Val
            100                 105                 110

Val Ala Pro Ser Leu Glu Val Tyr Val Asp His Ala Ser Leu Pro Thr
        115                 120                 125

```
Leu Gln Gln Leu Met Asp Ile Ile Lys Ser Glu Glu Glu Asn Pro Thr
            130                 135                 140

Ala Gln Arg Tyr Ile Ala Trp Gly Arg Ile Val Pro Thr Asp Glu Gln
145                 150                 155                 160

Met Lys Glu Leu Asn Ile Thr Ser Phe Ala Leu Ile Asn Asn His Thr
                165                 170                 175

Pro Ala Asp Leu Val Gln Glu Ile Val Lys Gln Ala Gln Thr Lys His
            180                 185                 190

Arg Leu Asn Val Lys Leu Ser Ser Asn Thr Ala His Ser Phe Asp Asn
        195                 200                 205

Leu Val Pro Ile Leu Lys Glu Leu Asn Ser Phe Asn Asn Val Thr Val
210                 215                 220

Thr Asn Ile Asp Leu Tyr Asp Asp Gly Ser Ala Glu Tyr Val Asn Leu
225                 230                 235                 240

Tyr Asn Trp Arg Asp Thr Leu Asn Lys Thr Asp Asn Leu Lys Ile Gly
                245                 250                 255

Lys Asp Tyr Leu Glu Asp Val Ile Asn Gly Ile Asn Glu Asp Thr Ser
            260                 265                 270

Asn Thr Gly Thr Ser Ser Val Tyr Asn Trp Gln Lys Leu Tyr Pro Ala
        275                 280                 285

Asn Tyr His Phe Leu Arg Lys Asp Tyr Leu Thr Leu Glu Pro Ser Leu
290                 295                 300

His Glu Leu Arg Asp Tyr Ile Gly Asp Ser Leu Lys Gln Met Gln Trp
305                 310                 315                 320

Asp Gly Phe Lys Lys Phe Asn Ser Lys Gln Gln Glu Leu Phe Leu Ser
                325                 330                 335

Ile Val Asn Phe Asp Lys Gln Lys Leu Gln Asn Glu Tyr Asn Ser Ser
            340                 345                 350

Asn Leu Pro Asn Phe Val Phe Thr Gly Thr Thr Val Trp Ala Gly Asn
        355                 360                 365

His Glu Arg Glu Tyr Tyr Ala Lys Gln Gln Ile Asn Val Ile Asn Asn
370                 375                 380

Ala Ile Asn Glu Ser Ser Pro His Tyr Leu Gly Asn Ser Tyr Asp Leu
385                 390                 395                 400

Phe Phe Lys Gly His Pro Gly Gly Ile Ile Asn Thr Leu Ile Met
                405                 410                 415

Gln Asn Tyr Pro Ser Met Val Asp Ile Pro Ser Lys Ile Ser Phe Glu
            420                 425                 430

Val Leu Met Met Thr Asp Met Leu Pro Asp Ala Val Ala Gly Ile Ala
        435                 440                 445

Ser Ser Leu Tyr Phe Thr Ile Pro Ala Glu Lys Ile Lys Phe Ile Val
450                 455                 460

Phe Thr Ser Thr Glu Thr Ile Thr Asp Arg Glu Thr Ala Leu Arg Ser
465                 470                 475                 480

Pro Leu Val Gln Val Met Ile Lys Leu Gly Ile Val Lys Glu Glu Asn
                485                 490                 495

Val Leu Phe Trp Ala Asp Leu Pro Asn Cys Glu Thr Gly Val Cys Ile
            500                 505                 510

Ala Val

<210> SEQ ID NO 3
<211> LENGTH: 1497
<212> TYPE: DNA
<213> ORGANISM: Photobacterium sp.
<220> FEATURE:
```

<221> NAME/KEY: CDS
<222> LOCATION: (1)..(1497)
<223> OTHER INFORMATION: alpha-2,6-sialyltransferase

<400> SEQUENCE: 3

```
atg tca gaa gaa aat aca caa tct att att aaa aat gat att aat aaa      48
Met Ser Glu Glu Asn Thr Gln Ser Ile Ile Lys Asn Asp Ile Asn Lys
1               5                   10                  15 act att att gat gag gag tat gtt aat tta gag cca att aat caa tca      96
Thr Ile Ile Asp Glu Glu Tyr Val Asn Leu Glu Pro Ile Asn Gln Ser
            20                  25                  30 aac atc tct ttt aca aaa cac tct tgg gta caa act tgt ggt acg caa     144
Asn Ile Ser Phe Thr Lys His Ser Trp Val Gln Thr Cys Gly Thr Gln
        35                  40                  45 caa cta tta aca gaa caa aat aaa gag tca ata tca tta tct gta gtg     192
Gln Leu Leu Thr Glu Gln Asn Lys Glu Ser Ile Ser Leu Ser Val Val
    50                  55                  60 gcg cca cga tta gat gac gat gaa aag tac tgc ttt gat ttt aat ggt     240
Ala Pro Arg Leu Asp Asp Asp Glu Lys Tyr Cys Phe Asp Phe Asn Gly
65                  70                  75                  80 gtt agt aat aaa ggt gaa aaa tat ata aca aaa gta aca tta aac gta     288
Val Ser Asn Lys Gly Glu Lys Tyr Ile Thr Lys Val Thr Leu Asn Val
                85                  90                  95 gtg gct cca tct tta gag gtt tat gtt gat cat gca tct ctt cca act     336
Val Ala Pro Ser Leu Glu Val Tyr Val Asp His Ala Ser Leu Pro Thr
            100                 105                 110 ctt cag cag cta atg gat att att aaa tcg gaa gaa gaa aat cct aca     384
Leu Gln Gln Leu Met Asp Ile Ile Lys Ser Glu Glu Glu Asn Pro Thr
        115                 120                 125 gca caa aga tat ata gct tgg ggg aga ata gtt ccg act gat gag caa     432
Ala Gln Arg Tyr Ile Ala Trp Gly Arg Ile Val Pro Thr Asp Glu Gln
    130                 135                 140 atg aaa gag tta aat att aca tcg ttt gca ttg ata aat aac cat aca     480
Met Lys Glu Leu Asn Ile Thr Ser Phe Ala Leu Ile Asn Asn His Thr
145                 150                 155                 160 cca gct gac tta gta caa gaa att gtt aag caa gca caa aca aag cat     528
Pro Ala Asp Leu Val Gln Glu Ile Val Lys Gln Ala Gln Thr Lys His
                165                 170                 175 aga ttg aat gtt aaa ctt agc tct aac act gct cat tca ttt gat aat     576
Arg Leu Asn Val Lys Leu Ser Ser Asn Thr Ala His Ser Phe Asp Asn
            180                 185                 190 tta gtg cca ata cta aaa gaa tta aat tcg ttt aat aac gtt acg gta     624
Leu Val Pro Ile Leu Lys Glu Leu Asn Ser Phe Asn Asn Val Thr Val
        195                 200                 205 aca aat ata gat tta tat gat gat ggt tca gca gaa tat gta aat tta     672
Thr Asn Ile Asp Leu Tyr Asp Asp Gly Ser Ala Glu Tyr Val Asn Leu
    210                 215                 220 tat aac tgg aga gat aca tta aat aaa aca gat aat tta aaa att ggt     720
Tyr Asn Trp Arg Asp Thr Leu Asn Lys Thr Asp Asn Leu Lys Ile Gly
225                 230                 235                 240 aaa gat tat ctt gag gat gtc att aat ggt atc aat gaa gac act tca     768
Lys Asp Tyr Leu Glu Asp Val Ile Asn Gly Ile Asn Glu Asp Thr Ser
                245                 250                 255 aat aca gga aca tca tct gtt tat aac tgg caa aaa cta tat cca gct     816
Asn Thr Gly Thr Ser Ser Val Tyr Asn Trp Gln Lys Leu Tyr Pro Ala
            260                 265                 270 aac tac cat ttt tta aga aaa gat tat tta act tta gaa cca tca tta     864
Asn Tyr His Phe Leu Arg Lys Asp Tyr Leu Thr Leu Glu Pro Ser Leu
        275                 280                 285 cat gag tta cga gac tat att ggt gat agt tta aag caa atg caa tgg     912
His Glu Leu Arg Asp Tyr Ile Gly Asp Ser Leu Lys Gln Met Gln Trp
```

```
                290                 295                 300
gat ggt ttc aaa aaa ttc aat agc aaa caa caa gaa tta ttc tta tcg      960
Asp Gly Phe Lys Lys Phe Asn Ser Lys Gln Gln Glu Leu Phe Leu Ser
305                 310                 315                 320 att gtt aat ttt gac aaa caa aaa tta caa aat gaa tat aat tca tct     1008
Ile Val Asn Phe Asp Lys Gln Lys Leu Gln Asn Glu Tyr Asn Ser Ser
                325                 330                 335 aat tta cca aac ttt gtg ttt aca ggt acg act gta tgg gct ggt aac     1056
Asn Leu Pro Asn Phe Val Phe Thr Gly Thr Thr Val Trp Ala Gly Asn
            340                 345                 350 cat gaa aga gag tat tat gcg aaa caa caa att aat gtc att aat aat     1104
His Glu Arg Glu Tyr Tyr Ala Lys Gln Gln Ile Asn Val Ile Asn Asn
        355                 360                 365 gca att aat gaa tcg agc cca cat tat tta ggc aat agt tat gat ttg     1152
Ala Ile Asn Glu Ser Ser Pro His Tyr Leu Gly Asn Ser Tyr Asp Leu
    370                 375                 380 ttc ttc aaa ggt cac cct ggt ggc ggt atc att aat aca tta ata atg     1200
Phe Phe Lys Gly His Pro Gly Gly Gly Ile Ile Asn Thr Leu Ile Met
385                 390                 395                 400 caa aac tat cct tca atg gtt gat att cca tca aaa ata tca ttt gaa     1248
Gln Asn Tyr Pro Ser Met Val Asp Ile Pro Ser Lys Ile Ser Phe Glu
                405                 410                 415 gtt ttg atg atg aca gat atg ctt cct gat gca gtt gct ggt ata gcg     1296
Val Leu Met Met Thr Asp Met Leu Pro Asp Ala Val Ala Gly Ile Ala
            420                 425                 430 agc tct tta tat ttc acg ata cca gct gaa aaa att aaa ttt ata gtt     1344
Ser Ser Leu Tyr Phe Thr Ile Pro Ala Glu Lys Ile Lys Phe Ile Val
        435                 440                 445 ttt aca tcg aca gaa act ata act gat cgt gaa act gct ttg aga agt     1392
Phe Thr Ser Thr Glu Thr Ile Thr Asp Arg Glu Thr Ala Leu Arg Ser
    450                 455                 460 cct tta gtt caa gta atg ata aaa cta ggt att gta aaa gaa gag aat     1440
Pro Leu Val Gln Val Met Ile Lys Leu Gly Ile Val Lys Glu Glu Asn
465                 470                 475                 480 gta ctt ttt tgg gct gat ctg cca aat tgt gaa aca ggt gtt tgt att     1488
Val Leu Phe Trp Ala Asp Leu Pro Asn Cys Glu Thr Gly Val Cys Ile
                485                 490                 495 gca gtc tag                                                         1497
Ala Val <210> SEQ ID NO 4
<211> LENGTH: 498
<212> TYPE: PRT
<213> ORGANISM: Photobacterium sp.

<400> SEQUENCE: 4

Met Ser Glu Glu Asn Thr Gln Ser Ile Ile Lys Asn Asp Ile Asn Lys
1               5                   10                  15

Thr Ile Ile Asp Glu Glu Tyr Val Asn Leu Glu Pro Ile Asn Gln Ser
            20                  25                  30

Asn Ile Ser Phe Thr Lys His Ser Trp Val Gln Thr Cys Gly Thr Gln
        35                  40                  45

Gln Leu Leu Thr Glu Gln Asn Lys Glu Ser Ile Ser Leu Ser Val Val
    50                  55                  60

Ala Pro Arg Leu Asp Asp Asp Glu Lys Tyr Cys Phe Asp Phe Asn Gly
65                  70                  75                  80

Val Ser Asn Lys Gly Glu Lys Tyr Ile Thr Lys Val Thr Leu Asn Val
                85                  90                  95

Val Ala Pro Ser Leu Glu Val Tyr Val Asp His Ala Ser Leu Pro Thr
```

```
                    100                 105                 110
Leu Gln Gln Leu Met Asp Ile Ile Lys Ser Glu Glu Asn Pro Thr
            115                 120                 125

Ala Gln Arg Tyr Ile Ala Trp Gly Arg Ile Val Pro Thr Asp Glu Gln
130                 135                 140

Met Lys Glu Leu Asn Ile Thr Ser Phe Ala Leu Ile Asn Asn His Thr
145                 150                 155                 160

Pro Ala Asp Leu Val Gln Glu Ile Val Lys Gln Ala Gln Thr Lys His
                165                 170                 175

Arg Leu Asn Val Lys Leu Ser Ser Asn Thr Ala His Ser Phe Asp Asn
            180                 185                 190

Leu Val Pro Ile Leu Lys Glu Leu Asn Ser Phe Asn Asn Val Thr Val
        195                 200                 205

Thr Asn Ile Asp Leu Tyr Asp Asp Gly Ser Ala Glu Tyr Val Asn Leu
    210                 215                 220

Tyr Asn Trp Arg Asp Thr Leu Asn Lys Thr Asp Asn Leu Lys Ile Gly
225                 230                 235                 240

Lys Asp Tyr Leu Glu Asp Val Ile Asn Gly Ile Asn Glu Asp Thr Ser
                245                 250                 255

Asn Thr Gly Thr Ser Ser Val Tyr Asn Trp Gln Lys Leu Tyr Pro Ala
            260                 265                 270

Asn Tyr His Phe Leu Arg Lys Asp Tyr Leu Thr Leu Glu Pro Ser Leu
        275                 280                 285

His Glu Leu Arg Asp Tyr Ile Gly Asp Ser Leu Lys Gln Met Gln Trp
    290                 295                 300

Asp Gly Phe Lys Lys Phe Asn Ser Lys Gln Gln Glu Leu Phe Leu Ser
305                 310                 315                 320

Ile Val Asn Phe Asp Lys Gln Lys Leu Gln Asn Glu Tyr Asn Ser Ser
                325                 330                 335

Asn Leu Pro Asn Phe Val Phe Thr Gly Thr Thr Val Trp Ala Gly Asn
            340                 345                 350

His Glu Arg Glu Tyr Tyr Ala Lys Gln Gln Ile Asn Val Ile Asn Asn
        355                 360                 365

Ala Ile Asn Glu Ser Ser Pro His Tyr Leu Gly Asn Ser Tyr Asp Leu
    370                 375                 380

Phe Phe Lys Gly His Pro Gly Gly Gly Ile Ile Asn Thr Leu Ile Met
385                 390                 395                 400

Gln Asn Tyr Pro Ser Met Val Asp Ile Pro Ser Lys Ile Ser Phe Glu
                405                 410                 415

Val Leu Met Met Thr Asp Met Leu Pro Asp Ala Val Ala Gly Ile Ala
            420                 425                 430

Ser Ser Leu Tyr Phe Thr Ile Pro Ala Glu Lys Ile Lys Phe Ile Val
        435                 440                 445

Phe Thr Ser Thr Glu Thr Ile Thr Asp Arg Glu Thr Ala Leu Arg Ser
    450                 455                 460

Pro Leu Val Gln Val Met Ile Lys Leu Gly Ile Val Lys Glu Glu Asn
465                 470                 475                 480

Val Leu Phe Trp Ala Asp Leu Pro Asn Cys Glu Thr Gly Val Cys Ile
                485                 490                 495

Ala Val

<210> SEQ ID NO 5
<211> LENGTH: 1500
<212> TYPE: DNA
```

<213> ORGANISM: Photobacterium sp.

<400> SEQUENCE: 5

```
attgaacgct ggcggcaggc ctaacacatg caagtcgagc ggtaacagat tgatagcttg    60
ctatcaatgc tgacgagcgg cggacgggtg agtaatgcct gggaatatac cctgatgtgg   120
gggataacta ttggaaacga tagctaatac cgcataatct cttcggagca aagaggggga   180
ccttcgggcc tctcgcgtca ggattagccc aggtgggatt agctagttgg tggggtaatg   240
gctcaccaag gcgacgatcc ctagctggtc tgagaggatg atcagccaca ctggaactga   300
gacacggtcc agactcctac gggaggcagc agtggggaat attgcacaat ggggggaaacc  360
ctgatgcagc catgccgcgt gtatgaagaa ggccttcggg ttgtaaagta ctttcagttg   420
tgaggaaggc agttaagtta atagcttagy tgtttgacgt tagcaacaga gaagcaccg    480
gctaactccg tgccagcagc cgcggtaata cggagggtgc gagcgttaat cggaattact   540
gggcgtaaag cgcatgcagg cggtctgtta agcaagatgt gaaagcccgg ggctcaacct   600
cggaacagca ttttgaactg gcagactaga gtcttgtaga gggggtaga  atttcaggtg   660
tagcggtgaa atgcgtagag atctgaagga ataccggtgg cgaaggcggc cccctggaca   720
aagactgacg ctcagatgcg aaagcgtggg gagcaaacag gattagatac cctggtagtc   780
cacgccgtaa acgatgtcta cttgaaggtt gtggccttga gccgtggctt tcggagctaa   840
cgcgttaagt agaccgcctg gggagtacgg tcgcaagatt aaaactcaaa tgaattgacg   900
ggggcccgca caagcggtgg agcatgtggt ttaattcgat gcaacgcgaa gaaccttacc   960
tactcttgac atccagagaa ttcgctagag atagcttagt gccttcggga actctgagac  1020
aggtgctgca tggctgtcgt cagctcgtgt tgtgaaatgt tgggttaagt cccgcaacga  1080
gcgcaaccct tatccttgtt tgccagcacg taatggtggg aactccaggg agactgccgg  1140
tgataaaccg gaggaaggtg gggacgacgt caagtcatca tggcccttac gagtagggct  1200
acacacgtgc tacaatggcg tatacagagg gctgcaaact agcgatagta agcgaatccc  1260
acaaagtacg tcgtagtccg gattggagtc tgcaactcga ctccatgaag tcggaatcgc  1320
tagtaatcgt gaatcagaat gtcacggtga atacgttccc gggccttgta cacaccgccc  1380
gtcacaccat gggagtgggc tgcaccagaa gtagatagct taaccttcgg gagggcgttt  1440
accacggtgt ggttcatgac tggggtgaag tcgtaacaag gtagccctag ggaacctgg   1500
```

<210> SEQ ID NO 6
<211> LENGTH: 22
<212> TYPE: DNA
<213> ORGANISM: Artificial
<220> FEATURE:
<223> OTHER INFORMATION: Synthetic primer ISH224-26ST-C3-R

<400> SEQUENCE: 6

```
ttcatcgtca tctaatcgtg gc                                              22
```

<210> SEQ ID NO 7
<211> LENGTH: 20
<212> TYPE: DNA
<213> ORGANISM: Artificial
<220> FEATURE:
<223> OTHER INFORMATION: Synthetic primer ISH224-26ST-C4-R

<400> SEQUENCE: 7

```
agttgttgcg taccacaagt                                                 20
```

<210> SEQ ID NO 8

```
<211> LENGTH: 31
<212> TYPE: DNA
<213> ORGANISM: Artificial
<220> FEATURE:
<223> OTHER INFORMATION: Synthetic primer ISH224-26ST-N0BspHI

<400> SEQUENCE: 8
agaatatcat gaaaaacttt ttattattaa c                              31

<210> SEQ ID NO 9
<211> LENGTH: 31
<212> TYPE: DNA
<213> ORGANISM: Artificial
<220> FEATURE:
<223> OTHER INFORMATION: Synthetic primer ISH224-26ST-N1PciI

<400> SEQUENCE: 9
cttgtaacat gtcagaagaa aatacacaat c                              31

<210> SEQ ID NO 10
<211> LENGTH: 33
<212> TYPE: DNA
<213> ORGANISM: Artificial
<220> FEATURE:
<223> OTHER INFORMATION: Synthetic primer ISH224-26ST-C0BamHI

<400> SEQUENCE: 10 tttttttggat ccctagactg caatacaaac acc                           33

<210> SEQ ID NO 11
<211> LENGTH: 1218
<212> TYPE: DNA
<213> ORGANISM: Photobacterium sp.
<220> FEATURE:
<221> NAME/KEY: CDS
<222> LOCATION: (1)..(1218)
<223> OTHER INFORMATION: alpha-2,6-sialyltransferase

<400> SEQUENCE: 11
```

| | | | | | | | | | | | | | | | | |
|---|---|---|---|---|---|---|---|---|---|---|---|---|---|---|---|---|
| atg | aac | gta | gtg | gct | cca | tct | tta | gag | gtt | tat | gtt | gat | cat | gca | tct | 48 |
| Met | Asn | Val | Val | Ala | Pro | Ser | Leu | Glu | Val | Tyr | Val | Asp | His | Ala | Ser | |
| 1 | | | | 5 | | | | | 10 | | | | | 15 | | |

| ctt | cca | act | ctt | cag | cag | cta | atg | gat | att | att | aaa | tcg | gaa | gaa | gaa | 96 |
|---|---|---|---|---|---|---|---|---|---|---|---|---|---|---|---|---|
| Leu | Pro | Thr | Leu | Gln | Gln | Leu | Met | Asp | Ile | Ile | Lys | Ser | Glu | Glu | Glu | |
| | | | 20 | | | | | 25 | | | | | 30 | | | |

| aat | cct | aca | gca | caa | aga | tat | ata | gct | tgg | ggg | aga | ata | gtt | ccg | act | 144 |
|---|---|---|---|---|---|---|---|---|---|---|---|---|---|---|---|---|
| Asn | Pro | Thr | Ala | Gln | Arg | Tyr | Ile | Ala | Trp | Gly | Arg | Ile | Val | Pro | Thr | |
| | | 35 | | | | | 40 | | | | | 45 | | | | |

| gat | gag | caa | atg | aaa | gag | tta | aat | att | aca | tcg | ttt | gca | ttg | ata | aat | 192 |
|---|---|---|---|---|---|---|---|---|---|---|---|---|---|---|---|---|
| Asp | Glu | Gln | Met | Lys | Glu | Leu | Asn | Ile | Thr | Ser | Phe | Ala | Leu | Ile | Asn | |
| 50 | | | | | 55 | | | | | 60 | | | | | | |

| aac | cat | aca | cca | gct | gac | tta | gta | caa | gaa | att | gtt | aag | caa | gca | caa | 240 |
|---|---|---|---|---|---|---|---|---|---|---|---|---|---|---|---|---|
| Asn | His | Thr | Pro | Ala | Asp | Leu | Val | Gln | Glu | Ile | Val | Lys | Gln | Ala | Gln | |
| 65 | | | | | 70 | | | | | 75 | | | | | 80 | |

| aca | aag | cat | aga | ttg | aat | gtt | aaa | ctt | agc | tct | aac | act | gct | cat | tca | 288 |
|---|---|---|---|---|---|---|---|---|---|---|---|---|---|---|---|---|
| Thr | Lys | His | Arg | Leu | Asn | Val | Lys | Leu | Ser | Ser | Asn | Thr | Ala | His | Ser | |
| | | | | 85 | | | | | 90 | | | | | 95 | | |

| ttt | gat | aat | tta | gtg | cca | ata | cta | aaa | gaa | tta | aat | tcg | ttt | aat | aac | 336 |
|---|---|---|---|---|---|---|---|---|---|---|---|---|---|---|---|---|
| Phe | Asp | Asn | Leu | Val | Pro | Ile | Leu | Lys | Glu | Leu | Asn | Ser | Phe | Asn | Asn | |
| | | | 100 | | | | | 105 | | | | | 110 | | | |

| gtt | acg | gta | aca | aat | ata | gat | tta | tat | gat | gat | ggt | tca | gca | gaa | tat | 384 |
|---|---|---|---|---|---|---|---|---|---|---|---|---|---|---|---|---|
| Val | Thr | Val | Thr | Asn | Ile | Asp | Leu | Tyr | Asp | Asp | Gly | Ser | Ala | Glu | Tyr | |
| | | 115 | | | | | 120 | | | | | 125 | | | | |

| gta | aat | tta | tat | aac | tgg | aga | gat | aca | tta | aat | aaa | aca | gat | aat | tta | 432 |
|---|---|---|---|---|---|---|---|---|---|---|---|---|---|---|---|---|
| Val | Asn | Leu | Tyr | Asn | Trp | Arg | Asp | Thr | Leu | Asn | Lys | Thr | Asp | Asn | Leu | |

```
                     130                 135                 140
aaa att ggt aaa gat tat ctt gag gat gtc att aat ggt atc aat gaa      480
Lys Ile Gly Lys Asp Tyr Leu Glu Asp Val Ile Asn Gly Ile Asn Glu
145                 150                 155                 160 gac act tca aat aca gga aca tca tct gtt tat aac tgg caa aaa cta      528
Asp Thr Ser Asn Thr Gly Thr Ser Ser Val Tyr Asn Trp Gln Lys Leu
                165                 170                 175 tat cca gct aac tac cat ttt tta aga aaa gat tat tta act tta gaa      576
Tyr Pro Ala Asn Tyr His Phe Leu Arg Lys Asp Tyr Leu Thr Leu Glu
            180                 185                 190 cca tca tta cat gag tta cga gac tat att ggt gat agt tta aag caa      624
Pro Ser Leu His Glu Leu Arg Asp Tyr Ile Gly Asp Ser Leu Lys Gln
        195                 200                 205 atg caa tgg gat ggt ttc aaa aaa ttc aat agc aaa caa caa gaa tta      672
Met Gln Trp Asp Gly Phe Lys Lys Phe Asn Ser Lys Gln Gln Glu Leu
    210                 215                 220 ttc tta tcg att gtt aat ttt gac aaa caa aaa tta caa aat gaa tat      720
Phe Leu Ser Ile Val Asn Phe Asp Lys Gln Lys Leu Gln Asn Glu Tyr
225                 230                 235                 240 aat tca tct aat tta cca aac ttt gtg ttt aca ggt acg act gta tgg      768
Asn Ser Ser Asn Leu Pro Asn Phe Val Phe Thr Gly Thr Thr Val Trp
                245                 250                 255 gct ggt aac cat gaa aga gag tat tat gcg aaa caa caa att aat gtc      816
Ala Gly Asn His Glu Arg Glu Tyr Tyr Ala Lys Gln Gln Ile Asn Val
            260                 265                 270 att aat aat gca att aat gaa tcg agc cca cat tat tta ggc aat agt      864
Ile Asn Asn Ala Ile Asn Glu Ser Ser Pro His Tyr Leu Gly Asn Ser
        275                 280                 285 tat gat ttg ttc ttc aaa ggt cac cct ggt ggc ggt atc att aat aca      912
Tyr Asp Leu Phe Phe Lys Gly His Pro Gly Gly Gly Ile Ile Asn Thr
    290                 295                 300 tta ata atg caa aac tat cct tca atg gtt gat att cca tca aaa ata      960
Leu Ile Met Gln Asn Tyr Pro Ser Met Val Asp Ile Pro Ser Lys Ile
305                 310                 315                 320 tca ttt gaa gtt ttg atg atg aca gat atg ctt cct gat gca gtt gct     1008
Ser Phe Glu Val Leu Met Met Thr Asp Met Leu Pro Asp Ala Val Ala
                325                 330                 335 ggt ata gcg agc tct tta tat ttc acg ata cca gct gaa aaa att aaa     1056
Gly Ile Ala Ser Ser Leu Tyr Phe Thr Ile Pro Ala Glu Lys Ile Lys
            340                 345                 350 ttt ata gtt ttt aca tcg aca gaa act ata act gat cgt gaa act gct     1104
Phe Ile Val Phe Thr Ser Thr Glu Thr Ile Thr Asp Arg Glu Thr Ala
        355                 360                 365 ttg aga agt cct tta gtt caa gta atg ata aaa cta ggt att gta aaa     1152
Leu Arg Ser Pro Leu Val Gln Val Met Ile Lys Leu Gly Ile Val Lys
    370                 375                 380 gaa gag aat gta ctt ttt tgg gct gat ctg cca aat tgt gaa aca ggt     1200
Glu Glu Asn Val Leu Phe Trp Ala Asp Leu Pro Asn Cys Glu Thr Gly
385                 390                 395                 400 gtt tgt att gca gtc tag                                             1218
Val Cys Ile Ala Val
                405

<210> SEQ ID NO 12
<211> LENGTH: 405
<212> TYPE: PRT
<213> ORGANISM: Photobacterium sp.

<400> SEQUENCE: 12

Met Asn Val Val Ala Pro Ser Leu Glu Val Tyr Val Asp His Ala Ser
1               5                   10                  15
```

Leu Pro Thr Leu Gln Gln Leu Met Asp Ile Ile Lys Ser Glu Glu Glu
            20                  25                  30

Asn Pro Thr Ala Gln Arg Tyr Ile Ala Trp Gly Arg Ile Val Pro Thr
                35                  40                  45

Asp Glu Gln Met Lys Glu Leu Asn Ile Thr Ser Phe Ala Leu Ile Asn
 50                  55                  60

Asn His Thr Pro Ala Asp Leu Val Gln Glu Ile Val Lys Gln Ala Gln
 65                  70                  75                  80

Thr Lys His Arg Leu Asn Val Lys Leu Ser Ser Asn Thr Ala His Ser
                85                  90                  95

Phe Asp Asn Leu Val Pro Ile Leu Lys Glu Leu Asn Ser Phe Asn Asn
                100                 105                 110

Val Thr Val Thr Asn Ile Asp Leu Tyr Asp Asp Gly Ser Ala Glu Tyr
                115                 120                 125

Val Asn Leu Tyr Asn Trp Arg Asp Thr Leu Asn Lys Thr Asp Asn Leu
130                 135                 140

Lys Ile Gly Lys Asp Tyr Leu Glu Asp Val Ile Asn Gly Ile Asn Glu
145                 150                 155                 160

Asp Thr Ser Asn Thr Gly Thr Ser Ser Val Tyr Asn Trp Gln Lys Leu
                165                 170                 175

Tyr Pro Ala Asn Tyr His Phe Leu Arg Lys Asp Tyr Leu Thr Leu Glu
                180                 185                 190

Pro Ser Leu His Glu Leu Arg Asp Tyr Ile Gly Asp Ser Leu Lys Gln
                195                 200                 205

Met Gln Trp Asp Gly Phe Lys Lys Phe Asn Ser Lys Gln Gln Glu Leu
210                 215                 220

Phe Leu Ser Ile Val Asn Phe Asp Lys Gln Lys Leu Gln Asn Glu Tyr
225                 230                 235                 240

Asn Ser Ser Asn Leu Pro Asn Phe Val Phe Thr Gly Thr Thr Val Trp
                245                 250                 255

Ala Gly Asn His Glu Arg Glu Tyr Tyr Ala Lys Gln Gln Ile Asn Val
                260                 265                 270

Ile Asn Asn Ala Ile Asn Glu Ser Ser Pro His Tyr Leu Gly Asn Ser
                275                 280                 285

Tyr Asp Leu Phe Phe Lys Gly His Pro Gly Gly Ile Ile Asn Thr
290                 295                 300

Leu Ile Met Gln Asn Tyr Pro Ser Met Val Asp Ile Pro Ser Lys Ile
305                 310                 315                 320

Ser Phe Glu Val Leu Met Met Thr Asp Met Leu Pro Asp Ala Val Ala
                325                 330                 335

Gly Ile Ala Ser Ser Leu Tyr Phe Thr Ile Pro Ala Glu Lys Ile Lys
                340                 345                 350

Phe Ile Val Phe Thr Ser Thr Glu Thr Ile Thr Asp Arg Glu Thr Ala
                355                 360                 365

Leu Arg Ser Pro Leu Val Gln Val Met Ile Lys Leu Gly Ile Val Lys
                370                 375                 380

Glu Glu Asn Val Leu Phe Trp Ala Asp Leu Pro Asn Cys Glu Thr Gly
385                 390                 395                 400

Val Cys Ile Ala Val
                405

<210> SEQ ID NO 13
<211> LENGTH: 1362
<212> TYPE: DNA

<213> ORGANISM: Photobacterium sp.
<220> FEATURE:
<221> NAME/KEY: CDS
<222> LOCATION: (1)..(1362)
<223> OTHER INFORMATION: alpha-2,6-sialyltransferase

<400> SEQUENCE: 13

```
atg acg caa caa cta tta aca gaa caa aat aaa gag tca ata tca tta        48
Met Thr Gln Gln Leu Leu Thr Glu Gln Asn Lys Glu Ser Ile Ser Leu
1               5                   10                  15 tct gta gtg gcg cca cga tta gat gac gat gaa aag tac tgc ttt gat        96
Ser Val Val Ala Pro Arg Leu Asp Asp Asp Glu Lys Tyr Cys Phe Asp
            20                  25                  30 ttt aat ggt gtt agt aat aaa ggt gaa aaa tat ata aca aaa gta aca       144
Phe Asn Gly Val Ser Asn Lys Gly Glu Lys Tyr Ile Thr Lys Val Thr
        35                  40                  45 tta aac gta gtg gct cca tct tta gag gtt tat gtt gat cat gca tct       192
Leu Asn Val Val Ala Pro Ser Leu Glu Val Tyr Val Asp His Ala Ser
    50                  55                  60 ctt cca act ctt cag cag cta atg gat att att aaa tcg gaa gaa gaa       240
Leu Pro Thr Leu Gln Gln Leu Met Asp Ile Ile Lys Ser Glu Glu Glu
65                  70                  75                  80 aat cct aca gca caa aga tat ata gct tgg ggg aga ata gtt ccg act       288
Asn Pro Thr Ala Gln Arg Tyr Ile Ala Trp Gly Arg Ile Val Pro Thr
                85                  90                  95 gat gag caa atg aaa gag tta aat att aca tcg ttt gca ttg ata aat       336
Asp Glu Gln Met Lys Glu Leu Asn Ile Thr Ser Phe Ala Leu Ile Asn
            100                 105                 110 aac cat aca cca gct gac tta gta caa gaa att gtt aag caa gca caa       384
Asn His Thr Pro Ala Asp Leu Val Gln Glu Ile Val Lys Gln Ala Gln
        115                 120                 125 aca aag cat aga ttg aat gtt aaa ctt agc tct aac act gct cat tca       432
Thr Lys His Arg Leu Asn Val Lys Leu Ser Ser Asn Thr Ala His Ser
    130                 135                 140 ttt gat aat tta gtg cca ata cta aaa gaa tta aat tcg ttt aat aac       480
Phe Asp Asn Leu Val Pro Ile Leu Lys Glu Leu Asn Ser Phe Asn Asn
145                 150                 155                 160 gtt acg gta aca aat ata gat tta tat gat gat ggt tca gca gaa tat       528
Val Thr Val Thr Asn Ile Asp Leu Tyr Asp Asp Gly Ser Ala Glu Tyr
                165                 170                 175 gta aat tta tat aac tgg aga gat aca tta aat aaa aca gat aat tta       576
Val Asn Leu Tyr Asn Trp Arg Asp Thr Leu Asn Lys Thr Asp Asn Leu
            180                 185                 190 aaa att ggt aaa gat tat ctt gag gat gtc att aat ggt atc aat gaa       624
Lys Ile Gly Lys Asp Tyr Leu Glu Asp Val Ile Asn Gly Ile Asn Glu
        195                 200                 205 gac act tca aat aca gga aca tca tct gtt tat aac tgg caa aaa cta       672
Asp Thr Ser Asn Thr Gly Thr Ser Ser Val Tyr Asn Trp Gln Lys Leu
    210                 215                 220 tat cca gct aac tac cat ttt tta aga aaa gat tat tta act tta gaa       720
Tyr Pro Ala Asn Tyr His Phe Leu Arg Lys Asp Tyr Leu Thr Leu Glu
225                 230                 235                 240 cca tca tta cat gag tta cga gac tat att ggt gat agt tta aag caa       768
Pro Ser Leu His Glu Leu Arg Asp Tyr Ile Gly Asp Ser Leu Lys Gln
                245                 250                 255 atg caa tgg gat ggt ttc aaa aaa ttc aat agc aaa caa caa gaa tta       816
Met Gln Trp Asp Gly Phe Lys Lys Phe Asn Ser Lys Gln Gln Glu Leu
            260                 265                 270 ttc tta tcg att gtt aat ttt gac aaa caa aaa tta caa aat gaa tat       864
Phe Leu Ser Ile Val Asn Phe Asp Lys Gln Lys Leu Gln Asn Glu Tyr
        275                 280                 285
```

```
aat tca tct aat tta cca aac ttt gtg ttt aca ggt acg act gta tgg      912
Asn Ser Ser Asn Leu Pro Asn Phe Val Phe Thr Gly Thr Thr Val Trp
    290                 295                 300 gct ggt aac cat gaa aga gag tat tat gcg aaa caa caa att aat gtc      960
Ala Gly Asn His Glu Arg Glu Tyr Tyr Ala Lys Gln Gln Ile Asn Val
305                 310                 315                 320 att aat aat gca att aat gaa tcg agc cca cat tat tta ggc aat agt     1008
Ile Asn Asn Ala Ile Asn Glu Ser Ser Pro His Tyr Leu Gly Asn Ser
                325                 330                 335 tat gat ttg ttc ttc aaa ggt cac cct ggt ggc ggt atc att aat aca     1056
Tyr Asp Leu Phe Phe Lys Gly His Pro Gly Gly Gly Ile Ile Asn Thr
    340                 345                 350 tta ata atg caa aac tat cct tca atg gtt gat att cca tca aaa ata     1104
Leu Ile Met Gln Asn Tyr Pro Ser Met Val Asp Ile Pro Ser Lys Ile
        355                 360                 365 tca ttt gaa gtt ttg atg atg aca gat atg ctt cct gat gca gtt gct     1152
Ser Phe Glu Val Leu Met Met Thr Asp Met Leu Pro Asp Ala Val Ala
370                 375                 380 ggt ata gcg agc tct tta tat ttc acg ata cca gct gaa aaa att aaa     1200
Gly Ile Ala Ser Ser Leu Tyr Phe Thr Ile Pro Ala Glu Lys Ile Lys
385                 390                 395                 400 ttt ata gtt ttt aca tcg aca gaa act ata act gat cgt gaa act gct     1248
Phe Ile Val Phe Thr Ser Thr Glu Thr Ile Thr Asp Arg Glu Thr Ala
                405                 410                 415 ttg aga agt cct tta gtt caa gta atg ata aaa cta ggt att gta aaa     1296
Leu Arg Ser Pro Leu Val Gln Val Met Ile Lys Leu Gly Ile Val Lys
            420                 425                 430 gaa gag aat gta ctt ttt tgg gct gat ctg cca aat tgt gaa aca ggt     1344
Glu Glu Asn Val Leu Phe Trp Ala Asp Leu Pro Asn Cys Glu Thr Gly
        435                 440                 445 gtt tgt att gca gtc tag                                             1362
Val Cys Ile Ala Val
    450

<210> SEQ ID NO 14
<211> LENGTH: 453
<212> TYPE: PRT
<213> ORGANISM: Photobacterium sp.

<400> SEQUENCE: 14

Met Thr Gln Gln Leu Leu Thr Glu Gln Asn Lys Glu Ser Ile Ser Leu
1               5                   10                  15

Ser Val Val Ala Pro Arg Leu Asp Asp Asp Glu Lys Tyr Cys Phe Asp
            20                  25                  30

Phe Asn Gly Val Ser Asn Lys Gly Glu Lys Tyr Ile Thr Lys Val Thr
        35                  40                  45

Leu Asn Val Val Ala Pro Ser Leu Glu Val Tyr Val Asp His Ala Ser
    50                  55                  60

Leu Pro Thr Leu Gln Gln Leu Met Asp Ile Ile Lys Ser Glu Glu
65                  70                  75                  80

Asn Pro Thr Ala Gln Arg Tyr Ile Ala Trp Gly Arg Ile Val Pro Thr
                85                  90                  95

Asp Glu Gln Met Lys Glu Leu Asn Ile Thr Ser Phe Ala Leu Ile Asn
            100                 105                 110

Asn His Thr Pro Ala Asp Leu Val Gln Glu Ile Val Lys Gln Ala Gln
        115                 120                 125

Thr Lys His Arg Leu Asn Val Lys Leu Ser Ser Asn Thr Ala His Ser
    130                 135                 140

Phe Asp Asn Leu Val Pro Ile Leu Lys Glu Leu Asn Ser Phe Asn Asn
```

```
                145                 150                 155                 160
Val Thr Val Thr Asn Ile Asp Leu Tyr Asp Asp Gly Ser Ala Glu Tyr
                    165                 170                 175

Val Asn Leu Tyr Asn Trp Arg Asp Thr Leu Asn Lys Thr Asp Asn Leu
                180                 185                 190

Lys Ile Gly Lys Asp Tyr Leu Glu Asp Val Ile Asn Gly Ile Asn Glu
            195                 200                 205

Asp Thr Ser Asn Thr Gly Thr Ser Ser Val Tyr Asn Trp Gln Lys Leu
        210                 215                 220

Tyr Pro Ala Asn Tyr His Phe Leu Arg Lys Asp Tyr Leu Thr Leu Glu
225                 230                 235                 240

Pro Ser Leu His Glu Leu Arg Asp Tyr Ile Gly Asp Ser Leu Lys Gln
                245                 250                 255

Met Gln Trp Asp Gly Phe Lys Lys Phe Asn Ser Lys Gln Gln Glu Leu
                    260                 265                 270

Phe Leu Ser Ile Val Asn Phe Asp Lys Gln Lys Leu Gln Asn Glu Tyr
                275                 280                 285

Asn Ser Ser Asn Leu Pro Asn Phe Val Phe Thr Gly Thr Thr Val Trp
        290                 295                 300

Ala Gly Asn His Glu Arg Glu Tyr Tyr Ala Lys Gln Gln Ile Asn Val
305                 310                 315                 320

Ile Asn Asn Ala Ile Asn Glu Ser Ser Pro His Tyr Leu Gly Asn Ser
                325                 330                 335

Tyr Asp Leu Phe Phe Lys Gly His Pro Gly Gly Gly Ile Ile Asn Thr
                340                 345                 350

Leu Ile Met Gln Asn Tyr Pro Ser Met Val Asp Ile Pro Ser Lys Ile
            355                 360                 365

Ser Phe Glu Val Leu Met Met Thr Asp Met Leu Pro Asp Ala Val Ala
        370                 375                 380

Gly Ile Ala Ser Ser Leu Tyr Phe Thr Ile Pro Ala Glu Lys Ile Lys
385                 390                 395                 400

Phe Ile Val Phe Thr Ser Thr Glu Thr Ile Thr Asp Arg Glu Thr Ala
                405                 410                 415

Leu Arg Ser Pro Leu Val Gln Val Met Ile Lys Leu Gly Ile Val Lys
                420                 425                 430

Glu Glu Asn Val Leu Phe Trp Ala Asp Leu Pro Asn Cys Glu Thr Gly
            435                 440                 445

Val Cys Ile Ala Val
        450

<210> SEQ ID NO 15
<211> LENGTH: 32
<212> TYPE: DNA
<213> ORGANISM: Artificial
<220> FEATURE:
<223> OTHER INFORMATION: Synthetic primer 224-26-N2Bsp

<400> SEQUENCE: 15
aaactttcat gacgcaacaa ctattaacag aa                              32

<210> SEQ ID NO 16
<211> LENGTH: 32
<212> TYPE: DNA
<213> ORGANISM: Artificial
<220> FEATURE:
<223> OTHER INFORMATION: Synthetic primer 224-26-N3Bsp

<400> SEQUENCE: 16
```

```
aagtaatcat gaacgtagtg gctccatctt ta                                32
```

<210> SEQ ID NO 17
<211> LENGTH: 32
<212> TYPE: DNA
<213> ORGANISM: Artificial
<220> FEATURE:
<223> OTHER INFORMATION: Synthetic primer 224-26-N3.1Bsp

<400> SEQUENCE: 17

```
cacgtgtcat gactcttcag cagctaatgg at                                32
```

<210> SEQ ID NO 18
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 18

```
Ser Glu Glu Asn Thr Gln Ser Ile Ile Lys Asn Asp Ile Asn Lys
1               5                   10                  15
```